United States Patent [19]
Remijan

[11] Patent Number: 4,541,697
[45] Date of Patent: * Sep. 17, 1985

[54] OPHTHALMIC TESTING DEVICES

[75] Inventor: Paul W. Remijan, Southbridge, Mass.

[73] Assignee: Randwal Instrument Co., Inc., Southbridge, Mass.

[*] Notice: The portion of the term of this patent subsequent to Oct. 18, 2000 has been disclaimed.

[21] Appl. No.: 494,712

[22] Filed: May 16, 1983

Related U.S. Application Data

[60] Continuation-in-part of Ser. No. 240,200, Mar. 3, 1981, Pat. No. 4,410,244, which is a division of Ser. No. 863,948, Dec. 23, 1977, Pat. No. 4,265,534.

[51] Int. Cl.⁴ .............................................. A61B 3/10
[52] U.S. Cl. .................................... 351/211; 351/205
[58] Field of Search ................ 351/211, 205, 214, 221

[56] References Cited
U.S. PATENT DOCUMENTS
4,009,940 3/1977 Ohzu .................................... 351/214

Primary Examiner—Rodney B. Bovernick
Attorney, Agent, or Firm—Cesari and McKenna

[57] ABSTRACT

Optical measuring and testing apparatus incorporates a holographically recorded, single-frequency, optically thin phase grating. When this phase grating is illuminated by a quasi-monochromatic, spatially coherent light source, it acts as a basic common path interferometer and constitutes a highly efficient source for a high contrast, stable, interference fringe pattern. Various apparatus embodiments incorporating the phase grating are described which permit (1) measurement of central and peripheral retinal acuity, (2) variable contrast testing to measure the ability of the eye to detect low contrast stimuli, (3) measurement of visually evoked responses to help diagnose retinal-neurological dysfunction, and (4) the testing of optical lenses.

43 Claims, 13 Drawing Figures

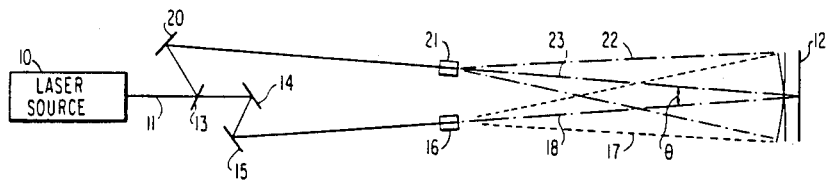

FIG. 2

STEP 1
EXPOSE PHOTOGRAPHIC EMULSION TO LASER TWO BEAM INTERFERENCE PATTERN

STEP 2
DEVELOP EMULSION

STEP 3
STOP DEVELOPMENT WITH ACID HARDENER

STEP 4
FIX AND HARDEN EMULSION

STEP 5
HYPO-CLEAR EMULSION

STEP 6
WASH EMULSION IN FILTERED WATER

STEP 7
RINSE EMULSION IN METHANOL TO REMOVE SENSITIZING DYE - THEN DRY

STEP 8
BLEACH EMULSION IN $Br_2$ VAPOR

STEP 9
RINSE EMULSION IN METHANOL TO REMOVE RESIDUAL $Br_2$ - THEN DRY

FIG. 5

A 

B 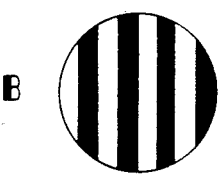

C 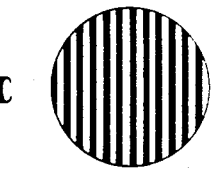

D 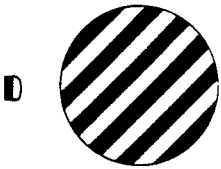

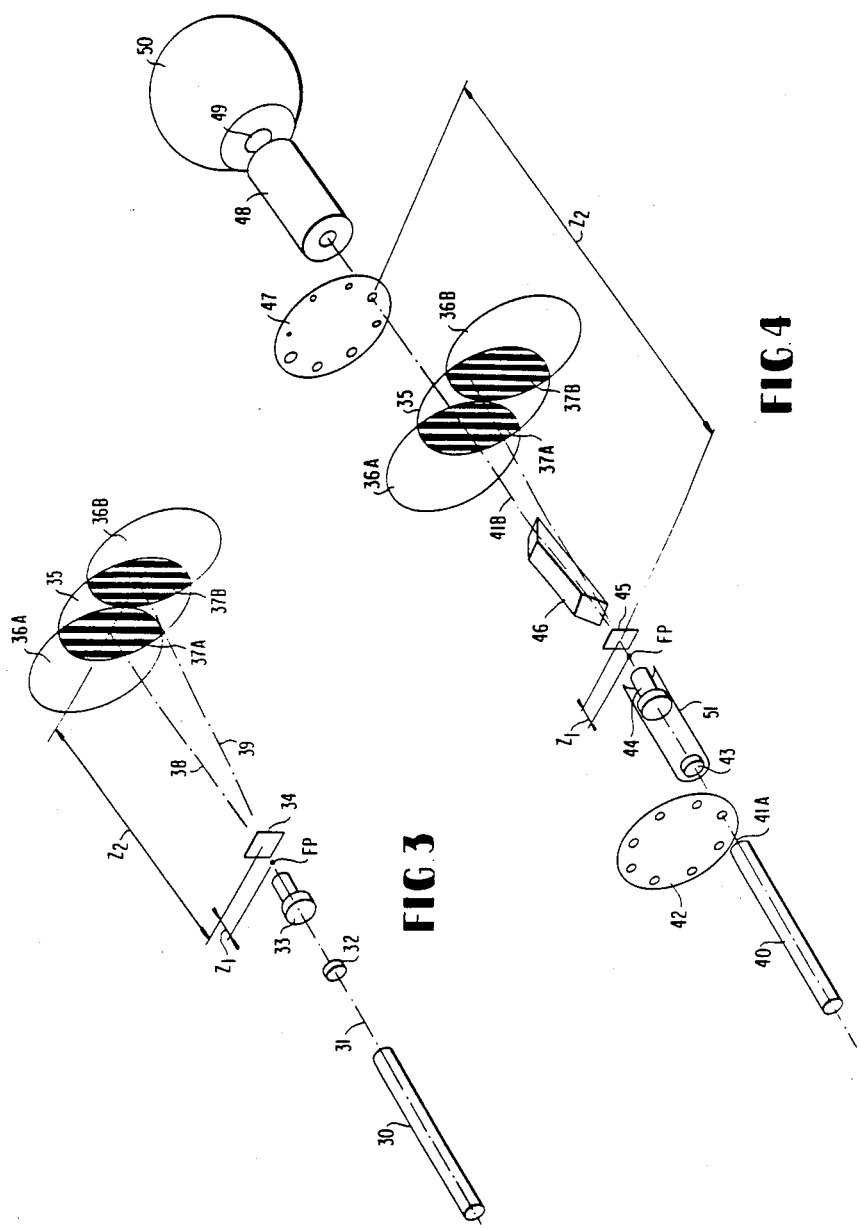

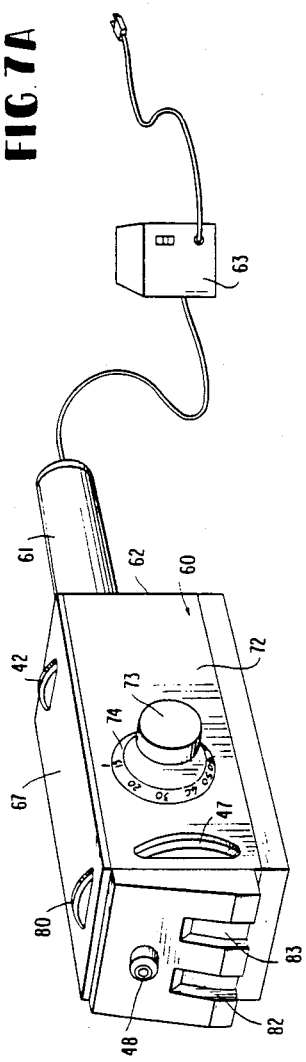
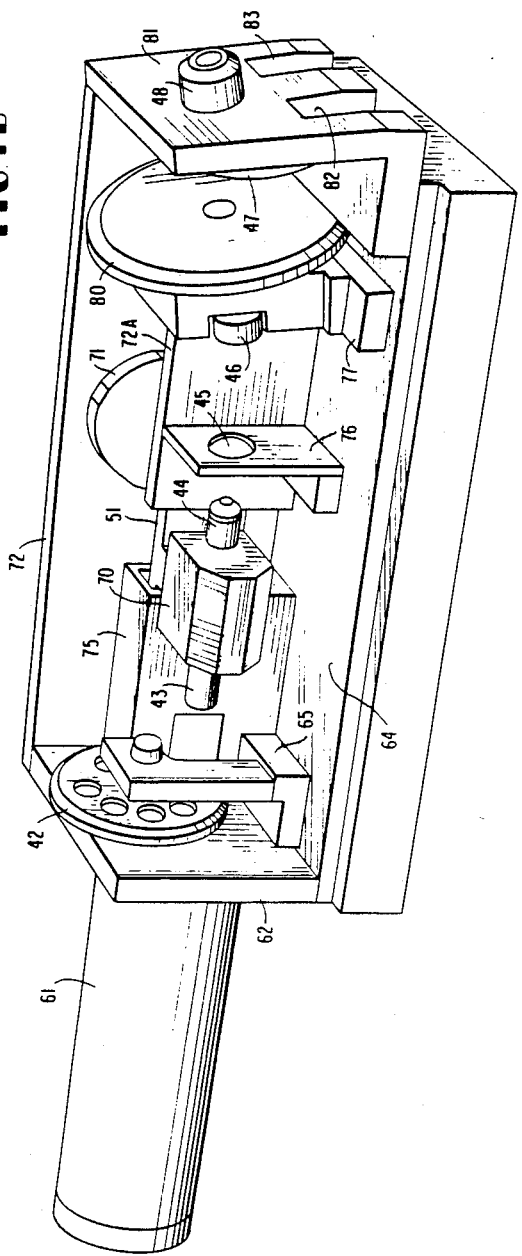
FIG. 7A
FIG. 7B

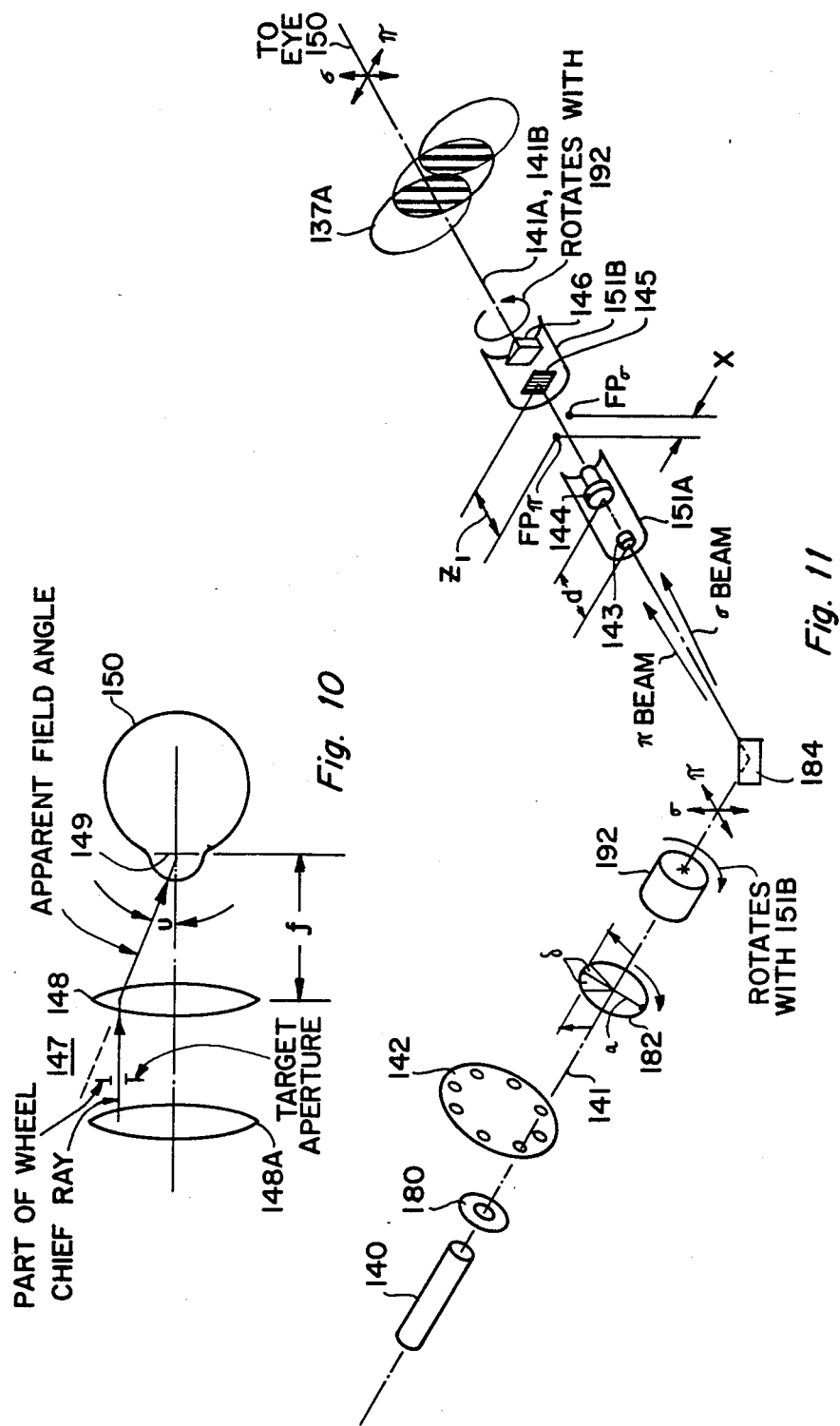

OPHTHALMIC TESTING DEVICES

CROSS REFERENCE TO RELATED APPLICATION

This is a continuation-in-part of my copending patent application Ser. No. 06/240,200, filed Mar. 3, 1981, now U.S. Pat. No. 4,410,244, issued Oct. 18, 1983, which is a division of my patent application Ser. No. 863,948, filed Dec. 23, 1977, now U.S. Pat. No. 4,265,534, issued May 5, 1981.

BACKGROUND OF THE INVENTION

This invention relates generally to the field of optical measuring and testing, and more specifically to apparatus incorporating interference fringe pattern generators for retinal acuity and related testing.

Ophthalmologists use a variety of techniques to measure ophthalmic and related functions and characteristics. Some of these measurements indicate retinal acuity at both the central and peripheral retinal regions. Others measure neurological response to a range of visual stimuli.

For example, ophthalmologists use apparatus of the type that implements either Moire or interference techniques to test and measure retinal acuity. This measurement is obtained by varying the "fineness" of the fringes projected onto the retina and monitoring the patient's ability to resolve them. The patient's ability to resolve a fringe pattern of a certain "fineness" converts directly into a measurement of retinal acuity.

Tests of peripheral vision can lead to an early diagnosis of glaucoma. Prior instruments of this general type used to measure the acuity of the central field of retina have not been employed successfully to measure the acuity of the eccentric region of the retina which is the area associated with peripheral vision. This is mainly because of their inability to project interference fringe patterns onto those eccentric regions of the retina, i.e. they do not have a sufficiently wide field. Resultantly, today, testing of peripheral vision is accomplished by flashing light at a variety of locations oblique to the patient's line of sight. The patient's ability or inability to detect those flashes at different points within a peripheral field of view is directly related to the size of the patient's visual field, but not necessarily to the acuity of the peripheral or eccentric regions of the retina. Therefore, such testing does not really provide an accurate indication of peripheral acuity.

Measurements of neurological response to spatially and temporally varying visual stimuli are useful in diagnosing other problems including retinal-neurological dysfunction. During testing, evoked potentials from the brain are produced in response to a visual stimulus. The most common visual stimulus today is a phase-reversing checkerboard or bar pattern displayed on a television screen.

All the foregoing tests and measurements using many current techniques require clear ocular media with reasonably normal refractive properties. If the media are not clear, as in the case of a patient afflicted with cataracts, the tests are not always valid. However, if a procedure were available for performing these tests independently of the opacity and refractive properties of the eye, better diagnosis could be made. Generally, laser produced interference fringe patterns provide a basis for instruments that measure retinal acuity because they can be projected onto the retina independently of ocular refractive errors and minor ocular media opacities.

There are two basic methods for producing fringe patterns: (1) an interferometric technique that utilizes interference phenomena, and (2) a Moire technique that utilizes shadow casting and/or pattern multiplication.

There are a wide variety of measuring and testing procedures that utilize interference fringe patterns and there are many ways to produce and control interference fringes. Generally, an interference fringe pattern is produced when at least two coherent beams of light are brought together and interact. When two coherent beams interact, they destructively interfere to produce dark spots or bands and constructively interfere to produce bright spots or bands.

Moire fringes are produced when two similar, geometrically regular patterns consisting of well defined clear and opaque areas are juxtaposed and transilluminated. Some examples of geometrically regular patterns used to generate Moire fringes include (1) Ronchi rulings, (2) sets of concentric circles, and (3) radial grids. The generation of Moire fringes can be considered as shadow casting; that is, the shadow of the first pattern falling onto the second pattern produces the Moire fringes. The mathematical function describing Moire fringes is obtained by multiplying the intensity transmissions or irradiances of the overlapped geometrically regular patterns.

Fringes generated by both interference and Moire techniques are used by ophthalmologists for testing retinal acuity. In one such apparatus, light from a laser is divided into two coherent beams by an optical element consisting of two adjoined dove prisms. These two beams are converged and directed into the eye where they interact to produce an interference fringe pattern on the retina.

In another apparatus used in the field of ophthalmology, a laser source and an ordinary Ronchi ruling form an interference fringe pattern. The laser source produces a laser beam that is directed to the Ronchi ruling. The Ronchi ruling splits the incident beam into multiple coherent beams of widely varying strengths. It is necessary to use complicated motions of numerous optical and mechanical components to select only two coherent beams and to control the spacing of interference fringes eventually projected onto the retina. In yet another ophthalmic apparatus, two Ronchi rulings are used that produce Moire fringes which are eventually imaged onto the retina.

Certain disadvantages exist in apparatus that utilize the interferometric techniques to form fringe patterns in ophthalmic applications. For example, in such apparatus the two light beams generally travel through different light paths that contain distinct optical elements. If the elements in each path are not matched optically, aberrations distort the fringe pattern. Matched optical elements can eliminate the aberration problem; however, they significantly increase the overall expense of the apparatus. Moreover, this apparatus is subject to various outside influences, such as vibration and thermal change. These influences can cause fringe pattern motion or noise and lead to improper measurements.

Moire techniques also have many limitations. When small spacings and high accuracies are required, the geometrically regular patterns used to generate Moire fringes are quite difficult and expensive to produce. In applications where one ruling moves next to a fixed ruling, the spacing between the rulings must be held constant or errors result. Also, Moire fringes are localized, i.e., they exist in a very small region of space, and additional optical components are often required to image the Moire fringes into desired regions.

Recently, an amplitude grating and a spatially coherent, quasi-monochromatic light source have been used to generate interference fringes. An amplitude grating is a generally transparent to semi-transparent media whose opacity is altered in accordance with some spatially periodic pattern. An amplitude grating "breaks up" or diffracts an incoming beam of light into a series of diffracted cones or orders. The strength, or amount, of light in each order depends upon the exact shape of the periodic opacity of the amplitude grating. Although various diffracted orders could be approximately the same strength, scalar diffraction theory for a thin amplitude grating predicts that the dominant strength will lie in the zero order undiffracted light and that the strength of other diffracted orders will vary. Indeed, practical applications bear out this prediction.

In U.S. Pat. No. 3,738,753, issued June 12, 1973, Huntley proposes to pass light from a source through an amplitude grating to produce different order cones of diffracted light: for example, zero order and first order cones. To compensate for the different intensities, the diffracted light cones are reflected back through the grating. After the second passage through the grating, the zero order cone of the reflected first order cone and the first order cone of the reflected zero order cone have equal strengths and are combined to form a high contrast interference fringe field. This double pass system is quite stable because it closely approximates a common path interferometer. In a common path interferometer, the interfering beams traverse the same optical path. Therefore, perturbations affect both beams simultaneously and do not distort the output fringe pattern which is sensitive only to differences between the two optical paths. However, problems in such a double pass system do occur because it is difficult to control grating substrate aberrations and mirror-grating separation.

Further improvements have been made with the advent of holographically produced amplitude gratings. Holographic amplitude gratings are produced by exposing a high resolution photographic emulsion to the precise interference pattern of a laser two-beam interferometer. During ordinary photographic processing, the photosensitive silver halide in the emulsion converts into opaque metallic silver to form the amplitude grating.

In an application of one such holographic grating, a double frequency holographic grating produces a so called "shearing" pattern. See U.S. Pat. No. 3,829,219, issued 1974 to Wyant, and U.S. Pat. No. 4,118,124 issued Oct. 3, 1978 to Matsuda. This grating is produced by sequentially exposing a single photographic emulsion to a first laser interference pattern of a first spatial frequency, $f_1$, and then to a second laser interference pattern of a second spatial frequency, $f_2$. Equal amplitude transmission modulations at both frequencies $f_1$ and $f_2$ are achieved by adjusting the exposure to the first and second laser patterns. Ordinarily, the two sequential exposures are identical, but if $f_1$ and $f_2$ are very different or if one laser pattern is in red light and the other is in green light, the sequential exposures must be compensated for the spectral and frequency responses of the photographic plate. These exposure adjustments to achieve equal amplitude transmission modulations in $f_1$ and $f_2$ are usually done by trial and error.

Upon illumination with spatially coherent, quasimonochromatic light, this double frequency grating produces two first order light cones of equal strength, one light cone being associated with each of the $f_1$ and $f_2$ frequencies. These two first order light cones interact to form a very stable, high contrast fringe pattern. Such a double frequency holographic shearing interferometer also is a common path interferometer. It is simple to construct. However, in this interferometer it is necessary to separate the zero order cone from the interacting first order cones. This separation requirement limits the f/number of the input light cone and the amount of shear obtainable. Moreover, if the two first order cones have high diffraction angles an astigmatic distortion of the output fringe field exists. In addition, the efficiency, or ratio of output fringe field power to input power, is only about 2%.

For many years people have bleached photographically recorded amplitude gratings to obtain "phase gratings". One basic type of such bleaching, known as volume bleaching, chemically converts the opaque silver in the photographic emulsion into a transparent, high index silver salt. A second type of bleaching, known as tanning, chemically removes the developed silver within the emulsion and leaves a void. A tanned phase grating has a corrugated surface. Whereas an amplitude grating selectively absorbs light, a bleached phase grating selectively introduces phase delays across the input light beam. As a result, a phase grating is much more efficient than an amplitude grating; that is, the ratio of first order power to input power is greater.

However, bleached gratings are generally characterized by substantial problems. They are very noisy and also may deteriorate physically back into amplitude gratings upon extended exposure to light. Bleached gratings also have a lower spatial frequency response than amplitude gratings. Although volume bleached gratings are less noisy and have a higher spatial frequency response than their tanned counterparts, they generally are weaker and less efficient.

The efficiency of a volume bleached grating can be increased by increasing its thickness. However, any substantial increase in thickness drastically changes the basic diffraction properties of the grating. Any amplitude or phase grating can be considered optically thick when the optical thickness of the emulsion is more than five times the grating spacing. A grating can be considered optically thin if the optical thickness of the emulsion is less than half the grating spacing. Properties of thick gratings are accurately predicted by electromagnetic theory, while properties of thin gratings are described by scalar diffraction theory. For example, a thick phase grating output consists of only the zero order and one first order diffracted cones. In addition, diffraction takes place only for a plane wave input at a certain specified angle with respect to the grating. On the other hand, a thin grating of the same spacing produces multiple orders (i.e. the 0, $\pm 1$, $\pm 2$, $\pm 3$, etc. orders) with either a spherical wave or plane wave input at an arbitrary angle with respect to the grating.

Distinctions between optically thin amplitude and optically thin phase gratings are accurately predicted by scalar diffraction theory. When a pure sinusoidal amplitude transmission perturbation exists in a thin amplitude grating, only the zero and $\pm 1$ diffracted orders exist. When a pure sinusoidal phase perturbation occurs in a thin phase grating, many orders (e.g., the 0, ±1, ±2, ±3, and other orders) are observed. The strengths of the phase grating orders are proportional to the normalized Bessel functions $[J_n(m/2)]^2$, where n is the order number (e.g., n equals 0, ±1, ±2, ...) and m is the strength, or magnitude, of the phase perturbation in radians. When the amplitude grating perturbation departs from a pure sinusoidal form, additional diffracted orders are generated. The strengths of these additional orders are directly related to the strengths of the Fourier components associated with the grating perturbation function.

With a phase grating, the diffracted orders associated with a non-sinusoidal phase perturbation are predicted by convolving the individual outputs from each Fourier component of the phase perturbation. Such a multiple convolution reveals complicated phase relationships between multiple orders associated with just one particular Fourier component. In addition, diffracted orders corresponding to sum and difference frequencies are generated when the phase perturbation consists of more than one fundamental spatial frequency. For example, one might consider bleaching the previously discussed double-frequency holographic grating to improve its poor efficiency. Although bleaching will increase the overall efficiency of such a grating, the bleached grating, in accordance with the convolutional operation, produces sum and difference frequency diffraction cones that are in addition to and that interact with the desired fundamental frequency diffraction cones. It is then possible for the sum and difference frequency diffraction cones to destroy the fringe field.

SUMMARY

Therefore, it is the object of this invention to provide an improved holographic phase grating for producing a high contrast interference pattern that is useful in ophthalmic applications.

Another object of this invention is to provide an improved holographic grating that is useful in the testing of retinal acuity.

Still another object of this invention is to provide an improved holographic phase grating that is useful in the testing of peripheral vision.

Still yet another object of this invention is to provide an improved holographic phase grating that is useful in the testing of visual evoked responses.

Yet another object of this invention is to provide apparatus for testing retinal acuity.

Yet still another object of this invention is to provide apparatus for testing peripheral retinal acuity.

Yet another object of this invention is to provide apparatus for testing visually evoked responses.

A further object is to provide apparatus in the nature of a focimeter for measuring the focal length of an optical element such as a lens and testing it for aberration.

In accordance with my invention, I use a single frequency holographic phase grating in ophthalmic testing equipment. A spatially coherent light source illuminates the grating to produce diverging diffractions, in conical or rectangular form, of different order. By "different order", I mean diffractions whose order numbers have different absolute values. In two diffractions of different order, the diffractions have equal strength and overlap thereby to produce a bright, high constrast, low noise interference pattern. I place a focusing element between the light source and grating to produce a spatially coherent source of light at a focal point that is slightly displaced from the grating. Other optical elements positioned in the resulting interference fringe field project the interference pattern through the eye and onto the retina.

Various controls in the optical path enable many ophthalmic measurements, including visual evoked response measurements and visual acuity measurements in the central and eccentric regions of the retina even in the presence of corneal or eye lens opacities known as cataracts, or other refractive effects.

The above and further objects and advantages of this invention may be better understood by referring to the following description taken in conjunction with the accompanying drawings.

BRIEF DESCRIPTION OF THE DRAWINGS

FIG. 1 is a diagram that illustrates the apparatus for producing a holographic grating in accordance with this invention;

FIG. 2 is a chart that depicts the various basic steps for processing a holographic grating in accordance with this invention;

FIG. 3 is a diagram of an interferometer constructed in accordance with one aspect of this invention for producing fringe patterns;

FIG. 4 is a diagram of apparatus constructed in accordance with this invention for measuring retinal acuity;

FIG. 5 depicts typical fringe patterns that are produced in the retinal acuity apparatus shown in FIG. 4;

FIG. 7A is a perspective view of a retinal acuity testing apparatus constructed in accordance with this invention;

FIG. 7B is a detailed perspective view of the apparatus shown in FIG. 7A with the housing partially removed;

FIG. 10 is a diagram that is useful in understanding peripheral acuity measurements;

FIG. 11 depicts, in diagrammatic form, another embodiment of ophthalmic testing apparatus for measuring acuity and for providing stimuli for visually evoked response measurements with variable contrast.

DESCRIPTION OF ILLUSTRATIVE EMBODIMENTS

A. Holographic Grating

Figure 6:
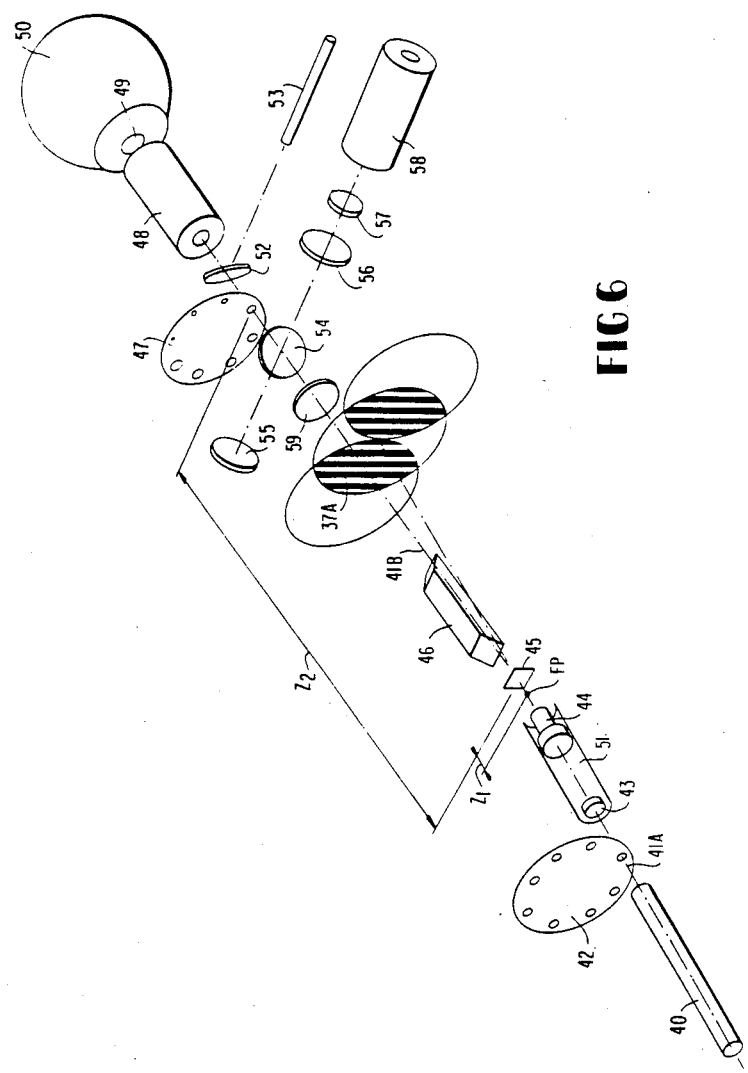
FIG. 6 is a diagram for an alternate embodiment of retinal acuity testing apparatus constructed in accordance with this invention.

FIG. 1 depicts, in diagrammatic form, the arrangement of apparatus necessary for exposing a photographic plate during the production of a holographic phase grating. The holographic phase grating produced in accordance with the arrangement shown in FIG. 1 and the procedures outlined in FIG. 2 are essential to the operation of the diverse embodiments of the invention that are shown in the other figures. Specifically, this apparatus includes a laser source 10 which directs light along an axis 11. The other apparatus in FIG. 1 splits the light into parts that travel over two separate paths and are then brought back together to expose a photographic plate 12.

A conventional beamsplitter 13 separates the light into two parts. A first part travels along a first path that includes mirrors 14 and 15 for reflecting the light into an objective lens and pinhole 16, thereby to produce a spherical wave that emanates from a point source at the pinhole. The wave appears in a cone 17 and is directed toward the photographic plate along an axis 18. The second path established by the beamsplitter 13 includes a mirror 20 and an objective lens and pinhole 21 that produce a spherical wave cone 22 that emanates from a point source at that pinhole along an axis 23. The light waves from these two point sources combine; they destructively interfere to produce dark bands and constructively interfere to produce bright bands at the photographic plate 12.

The photographic plate 12 mounts on a rotary table which positions the photographic plate 12 and accurately establishes an angle $\theta$ between the axes 18 and 23. The spatial frequency, $\delta$, of the interference pattern at plate 12 is closely approximated by the equation $$\delta = \frac{2 \sin (\theta/2)}{\lambda}, \tag{1}$$

where $\lambda$ is the laser wavelength. Although the fringes produced at the plate 12 are slightly hyperbolic, they are excellent approximations to rectilinear bands and therefore are shown as such in various figures. Increasingly better approximations to rectilinear bands are achieved by increasing the distance along the axes 18 and 23 between the plate 12 and the pinholes 16 and 21, respectively.

The apparatus diagrammed in FIG. 1 has been used to manufacture gratings having the desirable properties that characterize my invention. The equipment is simple and relatively inexpensive. For example, the laser 10 can comprise a TEM$_{00}$ mode laser; the beamsplitter 13, a conventional variable density beamsplitter that enables the intensity of the two beams to be equalized. The mirrors 14, 15 and 20 are standard planar mirrors. The objective lens comprises a conventional 10× microscope objective, and the pinhole matches that objective lens. The distances 18 and 23 are approximately 2 meters. With this specific arrangement, I am able to obtain a 500 line-per-millimeter interference fringe pattern over a 3"×3" area with maximum fringe displacement error of about 0.00254 millimeters.

Once the apparatus in FIG. 1 is arranged, the emulsion on the photographic film can be exposed to the interference pattern as shown as Step 1 in FIG. 2. During this exposure step, certain controls must be exercised to assure a holographic grating of good quality. For example, the exposure should be made in an environment that is not subjected to vibrations. Thermal disturbances should be minimized as any air flow between the beamsplitter 13 and the photographic plate 12 can distort the resulting fringes. In applications where very high densities and minimal distortions are required, the distances along axes 18 and 23 must be increased to 5 or even 10 meters. Precise determinations of $\lambda$ and $\theta$ must be made. Although this basic apparatus can be used to produce highly accurate holographic phase gratings, the maximum accuracy ultimately then will be determined by the accuracy of angular measuring equipment, the stability of the single frequency laser, the optical table stability, and the atmospheric and thermal controls that are exercised.

In order to produce a phase grating with special properties that enable the construction of the various disclosed embodiments, it is first necessary to produce an amplitude grating. Given the various properties of commercially available photographic emulsions and developers, a thin emulsion photographic plate and a chemically compatible developer are selected. A process of heavily overexposing and underdeveloping the emulsion reduces the optical thickness of the processed emulsion to a fraction of its original physical thickness. Thus, by utilizing the controls set forth in Steps 1 and 2 of FIG. 2, one produces an amplitude grating characterized by having:

1. an optically thin emulsion conforming to scalar diffraction theory;
2. a specific form for the absorbtion function which converts to a correspondingly specific phase transmission function after bleaching; and
3. a specific amplitude or strength of the absorbtion function which converts to a specific peak-to-peak phase modulation after bleaching.

Specific plate types, exposures, development times and developers are discussed later.

Once the development of step 2 is complete, the photographic plate is washed in an acid short-stop solution in Step 3. The solution contains an acid hardener. A two-minute treatment in a hardening bath produces acceptable results.

In Step 4, the emulsion of the photographic plate is fixed and hardened. A standard fixing bath and acid hardener have been used successfully, the plate being immersed in the bath for about ten minutes.

Next (Step 5), the emulsion is prewashed for thirty seconds and hypo-cleared in a hypo clearing bath for about two minutes. In Step 6, the emulsion is washed (e.g., twenty minutes ih filtered water) and then soaked in a methanol bath until all residual sensitizing dye is removed (Step 7). Once the methanol bath has been completed, the plate is dried in a light blow air drying operation.

All the foregoing steps are conventional photographic processing steps that utilize commercially available chemicals. Upon completion of Step 7, an amplitude grating has been produced. Steps 8 and 9 then convert this amplitude grating into a phase grating having the desired characteristics.

More specifically, after the photographic plate is dried thoroughly in step 7, it is bleached during Step 8 in a bromine vapor until the plate is clear. Once the bleaching operation has been completed, the plate is rinsed in a methanol bath to remove residual Br$_2$ and dried thoroughly by a light blow air drying operation in Step 9.

It now will be beneficial to discuss certain characteristics of these holographic phase gratings that are particularly desireable. First, the exposure and development times and the emulsion have been chosen to produce "thin" gratings. As a specific example, I have made 393.7 line-per-millimeter gratings on Kodak 131-01 plates according to the foregoing processing procedure using an average exposure of 200 ergs/cm$^2$ and a development time of 15 seconds in standard Kodak D-19 developer at 80° F. Uniform development is achieved by using a large development tank and rapid manual agitation of the plate. After complete processing in accordance with the steps of FIG. 2, the resulting thin phase grating diffracts both input spherical waves as well as input plane waves; as previously stated, a thick grating diffracts only input plane waves incident at a particular angle with respect to the grating.

Measurements have shown that a thin phase grating manufactured according to the foregoing process has a pure sinusoidal phase transmission function whose peak-to-peak phase delay produces equal strength zero and $\pm 1$ diffraction orders. The 200 ergs/cm$^2$ exposure produces an average amplitude transmission of approximately 0.45 for the developed, but unbleached, Kodak 131-01 plates. Experimental data has confirmed that a pure sinusoidal phase transmission function is maintained when the thin grating has an average amplitude transmission of 0.5 or less in its developed but unbleached state. The strength or peak-to-peak phase delay of the final phase grating is adjusted by controlling the initial exposure (Step 1, FIG. 2) within the limits set by an average amplitude transmission of 0.5 (measured after Step 7 in FIG. 2). A very weak phase grating produced with low exposure levels exhibits a strong zero order diffraction, a weak first order, and an even weaker second order diffraction. Stronger gratings produced with higher exposure levels exhibit increasingly more powerful first and second order diffractions and decreased zero order diffraction. Equal strength zero and $\pm 1$ diffraction orders or equal strength zero and $\pm 2$ diffraction orders are achieved by a trial and error adjustment of the initial exposure.

The advantages of such a thin phase grating that produces two different diffraction orders of equal strength will now become apparent in the following discussion of an interferometer that utilizes such a phase grating.

B. Interferometer

Referring now to FIG. 3, an interferometer is depicted in schematic form that includes a helium neon laser 30 which directs light along an axis 31 to a negative lens 32. The negative lens 32 expands the beam slightly so that it completely fills a microscope objective 33. The microscope objective 33 focuses this light at a focal point FP displaced a distance $Z_1$ from a holographic grating 34 constructed as described above. The laser 30, negative lens 32 and microscope objective 33 constitute a source of a quasi-monochromatic diverging spherical wave that emanates from the focal point FP. In one embodiment, the cone from the focal point FP is an f/2 cone.

When the spherical wave from the point source at the focal point FP strikes the grating 34, it produces a number of cones of diffraction. According to scalar diffraction theory, the strength of the diffracted cones is governed by the Bessel function $[J_n(m/2)]^2$ where n is the diffraction order number and m is the grating transmission function peak-to-peak phase delay in radians. The previously specified exposure and development times for a Kodak 131-01 plate yield a value of m=2.870 at $\lambda = 6328$ Å. The zero and first order diffraction cones are of equal intensity because $[J_0(1.435)]^2 = [J_1(1.435)]^2$. Moreover, the diffraction angles are such that the zero order cone overlaps both first order cones, while the first order cones merely abut each other. At some point at a distance $Z_2$ from the grating 34, an output such as is shown in FIG. 3 is produced. The zero order cone appears as planar circle 35; first order cones appear as planar circles 36A and 36B. Areas 37A and 37B are areas of overlap and the fringes are produced in those areas. Moreover, the fringes in the areas 37A and 37B are out of phase with each other. Thus, if the centrally located fringe in area 37A is a dark band, the corresponding fringe in area 37B is a light, or bright, band. By "light" and "dark" bands, I do not mean bands having the same intensity across the band, as the bands are shown in the drawings. The fringe intensity actually varies smoothly and is proportional to the square of a sine function, although the eye may perceive distinct alternating bands under some illumination conditions.

The 180° phase shift between the fringes in areas 37A and 37B is a direct result of having a pure sinusoidal phase transmission function associated with grating 34. When the phase transmission function of 34 departs from a pure sinusoid, the fringes in the areas 37A and 37B will have some other phase relationship not equal to 180°. The 180° phase shift is not essential to the production of high contrast fringe patterns; but it is important in a position detecting application where quadrature electrical signals are derived from the central fringes. Control of the grating transmission function form is achieved by selecting the proper combination of emulsion, developer, exposure and development time as previously discussed.

The interferometer shown in FIG. 3 has several properties. If the distance $Z_1$ is varied, the number of fringes within the overlap areas 37A and 37B changes. Specifically, decreasing the distance $Z_1$ decreases the number of fringes that appear in the overlap areas. As $Z_1$ is varied, fringes "flow" into or out of the areas 37A and 37B. Although this "fringe flow" may cause the central fringes to widen or narrow, it does not move the central fringes; they remain located at the centers of their respective areas. The importance of this central fringe behavior with $Z_1$ variations will be discussed later. If the grating 34 is moved in a plane that is normal to the axis 31 and perpendicular to the direction of the fringes, all the fringes in the areas 37A and 37B appear to slide through those areas, but the number of fringes in those areas remains unchanged. If the distance $Z_2$ varies, the number of fringes also remain the same, but in this case their sizes change, the fringe widths becoming smaller as $Z_2$ decreases. The interferometer parameters are related by the equation:

$$T = (Z_2 + Z_1)/\delta Z_1 \qquad (2)$$

Where T is the fringe period in overlap regions 37A and 37B, $\delta$ is the spatial frequency of the grating 34 defined by equation (1) and $Z_1$ and $Z_2$ are the positive distances shown in FIG. 3.

The holographic grating interferometer in FIG. 3 is very stable and free of fringe distortion from outside influences because it is essentially a common path interferometer. Atmospheric changes, air currents and thermal instabilities do not distort the fringes. Moreover, the intensity of the light in each of the diffraction cones is much greater than that usually obtained from amplitude gratings because the phase grating essentially is transparent and relies entirely on time delays within the grating 34 to produce the diffraction cones. As a result, the overall brightness of the fringe pattern is increased. Moreover, as the intensities in each of the zero-order and first-order cones are equal, the destructive and constructive interferences tend to be complete so the dark bands are essentially black, while the bright bands are essentially twice as bright as the average light. Thus the grating enables the production of a simple common path interferometer that produces bright, high-contrast fringes.

The foregoing properties lay a basis for understanding the application of a bleached phase grating in a retinal acuity tester. In this tester, the distance $Z_1$ is intentionally varied to change the number of fringes that appear in a given area and impinge the retina. Apparatus that is particularly adapted for use in a retinal acuity tester is discussed with reference to FIGS. 4 through 7B.

C. Retinal Acuity Tester

The retinal acuity tester in FIG. 4 includes a laser 40 that can comprise a low-power $TEM_{00}$ mode helium neon cylindrical laser, or other like laser. Light from the laser is directed along an axis 41A through a filter wheel 42. The filter wheel 42 contains a number of conventional metallic coated neutral density filters. These filters control the intensity of the light that is transmitted to the remaining elements in the retinal acuity tester. In this manner it is possible to control the brightness of the fringes eventually projected onto a patient's retina.

A negative lens 43 and microscope objective lens 44 that are movable along the axis 41A focus the light at a focal point FP. The negative lens 43 expands the beam from the laser slightly so as to completely fill the microscope objective lens 44 aperture with a uniform light distribution. A $-4$ mm focal length biconcave lens is a satisfactory negative lens. The microscope objective 44 is a conventional objective lens, a $10\times$ N.A. 0.25 objective lens being satisfactory.

The grating 45 comprises a holographically recorded, single frequency phase grating that is produced as described earlier. The grating frequency is 400 l/mm (lines per millimeter) to allow for ideal separation of zero and $\pm 1$ orders from the N.A. 0.25 objective input cone. The grating 45 also is optically thin, and the zero and first order diffractions have equal strengths. As becomes apparent later, there is no reason to control the phase of output fringes from the grating 45 when the grating is used in a retinal acuity testing apparatus. Therefore, the added constraints in the processing procedure associated with preserving a pure sinusoidal phase perturbation are eliminated. A convenient development time compatible with the requirement of producing an optically thin emulsion is chosen. Then exposure time is adjusted by trial and error until the desired strength of phase modulation is achieved. In this case, a modulation producing equal strength zero and $\pm 1$ orders is obtained. Thin, very clean, low noise, 400 l/mm phase gratings for the retinal acuity tester can be produced on Kodak 120-01 plates using an average exposure of 1000 ergs/cm$^2$ at 6328 Å. These plates are developed for 100 seconds Kodak D-19 developer at 68° F. (Steps 1 and 2 in FIG. 2). Steps 3 through 9 in FIG. 2 are used to complete the processing.

The grating 45 produces the diverging cones of different order diffractions. More specifically, there is a zero order cone represented by circle 35 and first order cones represented by abutting circles 36A and 36B. These cones are of equal strength so that they produce high contrast fringes as shown in areas 37A and 37B where the zero and first order cones overlap. In this specific embodiment, an axis 41B extends from the center of the grating 45 through the center of the area 37A. A dove prism 46 is positioned to receive the fringe field and is disposed with its longitudinal axis on the axis 41B. As the dove prism 46 is rotated about its longitudinal axis, the angle of fringe orientation within the fringe field 37A also rotates about the axis 41B through twice the prism rotation angle.

The fringe field propagates through the dove prism 46 to an aperture wheel 47. One aperture in the aperture wheel 47 is selectively aligned with the axis 41B by rotating the aperture wheel 47. An eyepiece 48 receives light transmitted through the selected aperture. This eyepiece 48 forms twin point sources within an eye pupil 49 of the patient. These point sources correspond to the point sources formed in FIG. 1 by the objective lenses and pinholes 16 and 21. The fringe field in the area 37A thereupon propagates through the eye and is projected onto the retina 50.

During testing, a patient positions his eye pupil 49 on the axis 41B near the eyepiece 48 to intercept the twin point sources from the eyepiece 48. When his eye is in the proper position, the patient will sense or "see" the fringe pattern projected onto his retina 50. The cornea and eye lens have negligible optical power in such an arrangement and therefore have a negligible effect upon the fringe pattern projected onto the retina.

The negative lens 43 and microscope objective 44 are positioned on a slider 51 that can be moved along the axis 41A thereby to reposition the focal point (FP) with respect to the grating 45. As the slider 51 and focal point (FP) are repositioned, the number of fringes within fringe field 37A changes. The ability of the patient to see or discern a pattern of a given number of fringes within the field projected onto his retina is directly equated to standard measurements of acuity.

During retinal examination the dove prism 46 and aperture wheel 47 play subtle, but important, roles because the retinal test is rather subjective. The examiner is able to control the orientation of the fringes by rotating the dove prism 46 thereby to determine whether a patient's claim of being able to see a pattern in a certain orientation is actually valid. To the extent that retinal response might exhibit orientational variations, the nature of such variations also can be evaluated.

The diameter of the aperture selected by positioning the aperture wheel 47 controls the size of the retinal area stimulated by the fringe pattern. This field control is important in determining the extent of any macular degeneration. The retinal fields offered by the various apertures in wheel 47 range, in one specific example, from 20° to 0.5°, these fields correspond to circular regions that are stimulated on the retina ranging from 5.0 to 0.155 mm. in diameter.

FIG. 5 illustrates a number of different patterns as they will be perceived by a patient who is being examined utilizing the apparatus shown in FIG. 4. If the slider 51 is located in an intermediate position, the patient could perceive the fringe pattern of alternate dark and bright bands that are shown as pattern A. If a laser that emits red light is used, the light areas are red and the dark areas are black. Thus, the patient perceives a series of straight red and black lines. If the slider 51 is moved along the axis 41A in FIG. 4 toward the grating 45, the number of fringes decreases and the patient perceives pattern B that contains fewer and wider fringes. Likewise, motion of the slider 51 in a direction away from the grating 45 beyond the intermediate position increases the number of fringes as shown in pattern C. If, on the other hand, the slider 51 is in the same position that produces pattern A, a 22.5° rotation of the dove prism 46 in FIG. 4 rotates the fringes 45° to an orientation shown in pattern D.

Another embodiment of the retinal acuity tester is shown in FIG. 6. This tester differs from the retinal acuity tester shown in FIG. 4 by the addition of a viewing system for the examiner. This viewing system can be added because the common path principle applies to the overlapped orders producing the area 37A. Various viewing system designs could be used because the choice of specific components is not dictated by fringe distortion considerations. However, the components of the viewing system should be of reasonable quality to insure best viewing system performance.

The viewing system as shown in FIG. 6 includes a beamsplitter 52 that is disposed between the aperture wheel 47 and the eyepiece 48. The beamsplitter 52 directs white light from a fiber optics light guide 53 through the eyepiece 48 onto the eye. The source of light for the light guide can comprise a standard low power fiber optics illuminator (not shown). Light reflected from the eye passes through the eyepiece 48, the beamsplitter 52 and the aperture in aperture wheel 47 aligned with the axis 41B to another beamsplitter 54. Normally the largest aperture is aligned to provide the largest field of view. The beamsplitter 54 directs this light to a concave mirror 55 that forms a real image of the eye surface near the beamsplitter 54. Lens 56 relays the real image of the eye surface through a polarizer 57 to the focal plane of an eyepiece 58 for observation. The polarizer 57 coacts with another crossed polarizer 59 between the dove prism 46 and the beamsplitter 54 to eliminate that portion of the fringe field reflected from beamsplitter 54 toward eyepiece 58. Viewing system aberrations are reduced by locating the aperture wheel 47 at the center of curvature of mirror 55 and using a symmetrical relay lens 56 at 1:1 conjugates.

Even with good chin rests one of the most frequently encountered problems in ophthalmic examinations is the proper positioning of the patient's eye. With a properly aligned viewing system of the type disclosed in FIG. 6, the exact center of the image observed through eyepiece 58 is centered between the twin coherent point sources formed by eyepiece 48. Thus, when the examiner properly positions a patient's eye pupil to intercept the twin coherent point sources, he will observe a clear, centralized image of the eye pupil through eyepiece 58. This viewing system is especially valuable for testing cataract patients, because it enables precise location of the twin coherent point sources at any existing opening in a cataract.

FIGS. 7A and 7B are two views of a retinal acuity tester constructed in accordance with this invention. This specific tester embodies the elements that are disclosed in FIG. 4. More specifically, the tester includes a housing 60 having a conventional laser unit 61 extending from one end 62 of the housing 60. The laser 61 is connected to a conventional laser power supply 63.

The various elements within the housing 60 are supported on a base plate 64. A first element includes an upright stand 65 that supports the filter wheel 42. The examiner rotates a portion of the circumference of the filter wheel 42 that extends through a slot in a top plate 67 of the housing 60 to position the appropriate filter on the light axis. Although the angular position of the filter wheel 42 might be maintained by friction, a more positive positioning means would incorporate some detent indexing mechanism for interacting between the upright stand 65 and the filter wheel 42.

The negative lens 43 and microscope objective lens 44 shown in FIG. 4 are mounted in a housing 70 carried on the slider 51. A rotary cam 71 has a shaft that extends through a side wall 72 of the housing 60 and is supported on a stand 72A. This shaft carries a positioning knob 73, a scale 74 and a detent mechanism that is not shown. The scale 74 is graduated directly in equivalent Snellen acuities ranging from 20/15 through 20/400. As the examiner rotates the knob 73, the cam 71 rotates and longitudinally displaces the slider 51 and both the negative lens 43 and the microscope objective lens 44 thereby to vary the position of the focal point FP shown in FIG. 4. In this embodiment, the slider 51 is constituted by a cam follower that contacts the cam 72 and is supported in a slide 75. The slide 75 also houses springs to bias the slider 51 against the cam 71.

Another upright stand 76 is mounted to the base plate 64. This stand 76 carries the grating 45. Thus, when the power supply 63 is activated, the light emanating from the laser 61 passes through the filter wheel 42, the negative lens 43, the microscope objective lens 44 to the grating 45 thereby to produce zero and first order diffraction cones that have equal strengths and that overlap. In one specific arrangement the distance between the grating 45 and the focal point varies over a range from about 0.6 mm to 25 mm. That range of distances enables the apparatus to produce fringe patterns that correspond to acuity measurements from 20/400 through 20/15.

There is also located at a fixed position on the base plate 64 another stand 77. This stand is skewed slightly with respect to the housing 60 in order to position the longitudinal axis of the dove prism 46 on the axis 41 B shown in FIG. 4. The stand 77 carries a rotatable wheel 80. A portion of the wheel 80 extends through another slot in the top 67. The wheel 80 carries the dove prism 46 so that rotation of the wheel 80 by the examiner rotates the dove prism 46 and changes the orientation of the fringes, as shown in pattern D of FIG. 5.

The next element in the tester is an end wall 81 that supports the aperture wheel 47 and the eyepiece 48 on the axis 41B in FIG. 4. A portion of the aperture wheel 47 extends through a slot in wall 60 allowing the examiner to center the various apertures on axis 41B shown in FIG. 4. In addition, the end wall 81 contains two notches 82 and 83 in an exterior portion of the wall. These notches are offset on opposite sides of the eyepiece 48. They allow the patient to position his nose with respect to the housing during examination. For example, the patient would position his nose in the notch 82 during examination of his right eye.

From the foregoing discussion, it will be apparent that the retinal acuity tester disclosed in FIGS. 7A and 7B is compact and easy to construct. All the optical elements, except the grating 45, are conventional elements that are readily available and relatively inexpensive. Such elements are used because the retinal acuity tester is an example of a common path interferometer and because the fringes are not subject to thermal variations, vibrations or other environmental perturbations.

D. White Light Source Acuity Tester

Figure 8:
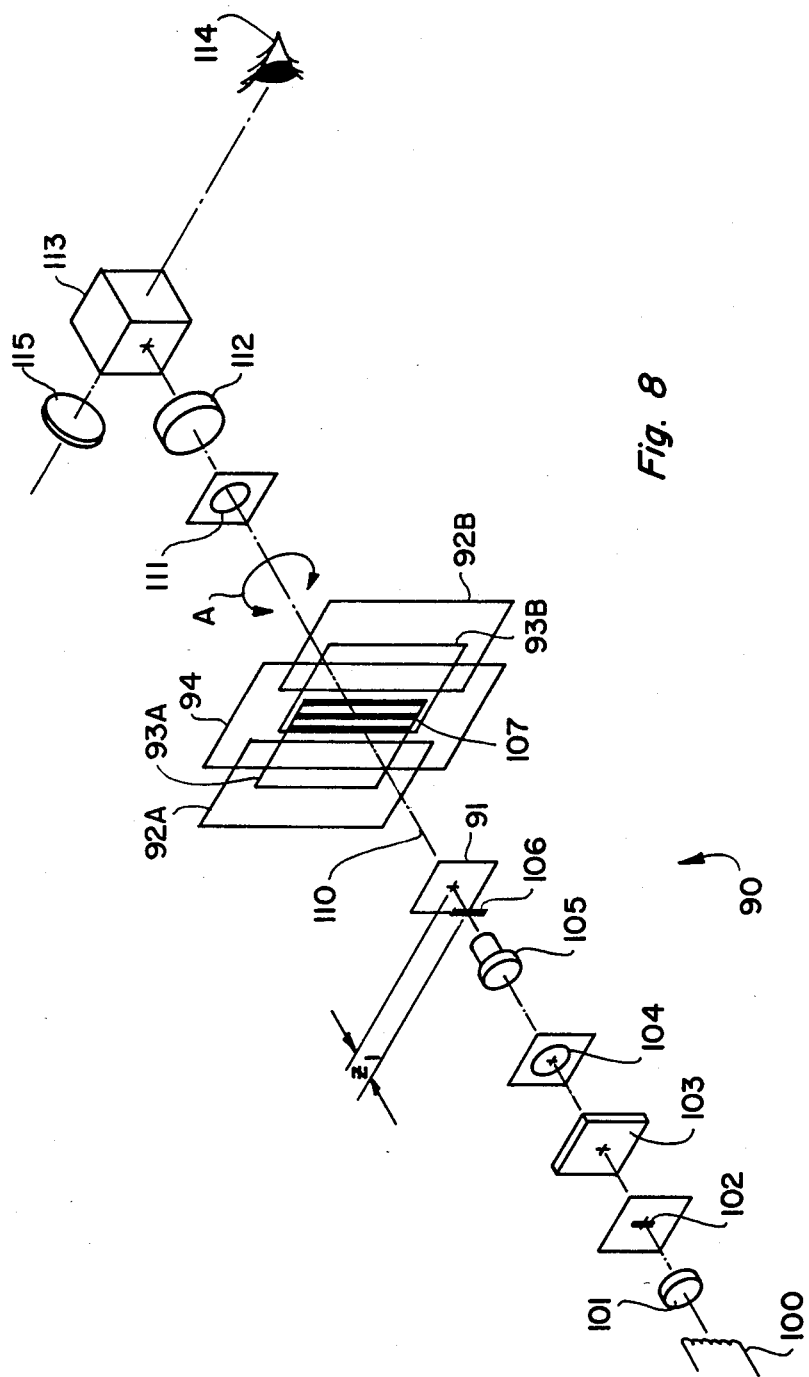
FIG. 8 depicts, in diagrammatic form, a retinal acuity tester that includes a white-light source.

Another embodiment of an ophthalmic device that uses the basic grating in an interferometer as shown in FIG. 3 is disclosed in FIG. 8. However, unlike the previously described figures, this apparatus uses "white light" rather than energy from a laser. More specifically, the disclosed white light retinal acuity instrument operates with a small, low voltage, filament lamp, thus eliminating the need for a laser and power supply. Moreover, it can be constructed as a hand-held instrument, thereby eliminating the need for head-chin rests, tables and other ancillary equipment. In comparison to the FIG. 3 version employing a laser light source, however, this instrument is less effective in penetrating cataracts in the patient's eye.

Referring to FIG. 8, a spatially coherent light source indicated generally at 90 illuminates a 350 l/mm holographic grating 91 to generate second order diffraction bands 92A, 92B, first order bands 93A, 93B and zero order band 94. The spatially coherent light source consists of filament lamp 100, collecting lens 101, and rectangular slit 102. Lamp 100 emits white light and lens 101 collects that light flux and maximizes the irradiance at slit 102. Slit 102 has a width that is compatible with the existence of spatially coherent light at aperture 104 of a microscope objective 105; a typical slit width is between 5 and 15 microns. Objective 105 is operated at a numerical aperture of about 1.3 times the $\delta\lambda$ product of the grating 91, $\delta$ being the grating spatial frequency and $\lambda \approx 5500$ Å for white light operation. Such a choice of numerical aperture maximizes the fringe overlap area 107. In FIG. 8, the fields or bands of fringes 92A, 92B, 93A, 93B and 94 are rectangular because of the presence of rectangular slit 102. Filter 103 is a simple, colored glass optical filter that limits the spectral content of the white light radiation. Microscope objective 105 forms a line image 106 of slit 102 which is aligned to parallel the grating structure.

The combination of the white light source 90 and holographic grating 91 is effective when the grating 91 diffracts all of the input energy at a particular wavelength out of the zero order. When this occurs, the area 107 is formed by the overlap of +1 and −1 diffracted orders. The physical dimensions of the area 107 are varied by adjusting the numerical aperture of objective 105 by means of aperture 104. Interference fringes formed in area 107 are achromatic since light of all wavelengths form fringes of the same spatial frequency. The angle between +1 and −1 order diffractions within area 107 is larger for longer (red) wavelengths and smaller for the shorter (blue) wavelengths. This effect is essentially counterbalanced by the requirement of larger interaction angles for longer wavelengths and smaller interaction angles for shorter wavelengths to produce fringes of the same spatial frequency. Also important is the symmetrical diffraction of +1 and −1 order energy about an optical axis 110, thereby causing the fringe patterns associated with each wavelength to be in register or in phase, as well as being at the same spatial frequency.

Achromatic fringes within fringe field 107 project to aperture 111 located at the front focal plane of eyepiece lens 112. Lens 112, acting via a reflection from cube beamsplitter 113 forms multiple chromatic images of the line source 102 in the pupillary region of the patient's eye 114. The achromatic fringe pattern then projects onto the retina, unaberrated by the eye's refractive error. Aperture 111 limits the fringe field size perceived by the patient. Beamsplitter cube 113 and a lens 115 allow the examiner to monitor penetration of light energy at the patient's pupil. Lens 115 acts as a simple magnifying glass focused at the patient's pupillary area.

The spatial frequency of achromatic fringes perceived by the patient is controlled by varying the distance $Z_1$ between the line image 106 and grating 91. Fringe orientation perceived by the patient is altered by rotating the entire light source 90, grating 91, aperture 111 and lens 112 in unison about the axis 110 as shown by the double headed arrow A.

As previously indicated, optimum results with the white light retinal acuity instrument are achieved when energy in the zero order diffraction area 94 is minimized. According to scalar diffraction theory, for any wavelength, an optically thin phase grating with a purely sinusoidal peak-to-peak phase delay of 4.8 radians extinguishes all energy in the zero order diffraction. However, for a given grating which has fixed characteristics, compete extinction of the zero order diffraction is not possible for a range of wavelengths since the phase delay of 4.8 radians is wavelength dependent. Therefore, the grating 91 is manufactured with a peak-to-peak phase delay of 4.8 radians at the wavelength associated with optimum eye sensitivity.

To summarize, high contrast achromatic fringes are achieved when the grating 91 has the following characteristics:

1. the emulsion is optically thin and conforms to scalar diffraction theory;
2. the phase perturbation function is purely sinusoidal; and
3. the peak-to-peak phase delay is 4.8 radians at the wavelength of maximum eye sensitivity.

A grating with these characteristics can be exposed and developed according to the procedures of FIG. 2.

The preferred embodiment of the hand held instrument pictured in FIG. 8 includes a thin, holographic, single frequency phase grating which extinguishes zero order energy at about 5500 Å, the most sensitive region of the visible spectrum. Filter 103 is chosen to pass wavelengths near the wavelength of zero order extinction. Experiments on a prototype instrument have confirmed that even with a moderate passband of 1000 Å, centered at the zero order extinction wavelength, nearly "white light" fringes of very high contrast, 0.9 or better, are typical. As the passband of filter 103 is increased, the fringe contrast diminishes due to an increase in zero order diffracted energy. However, even without a filter, fringe contrast is quite acceptable.

Figure 9:
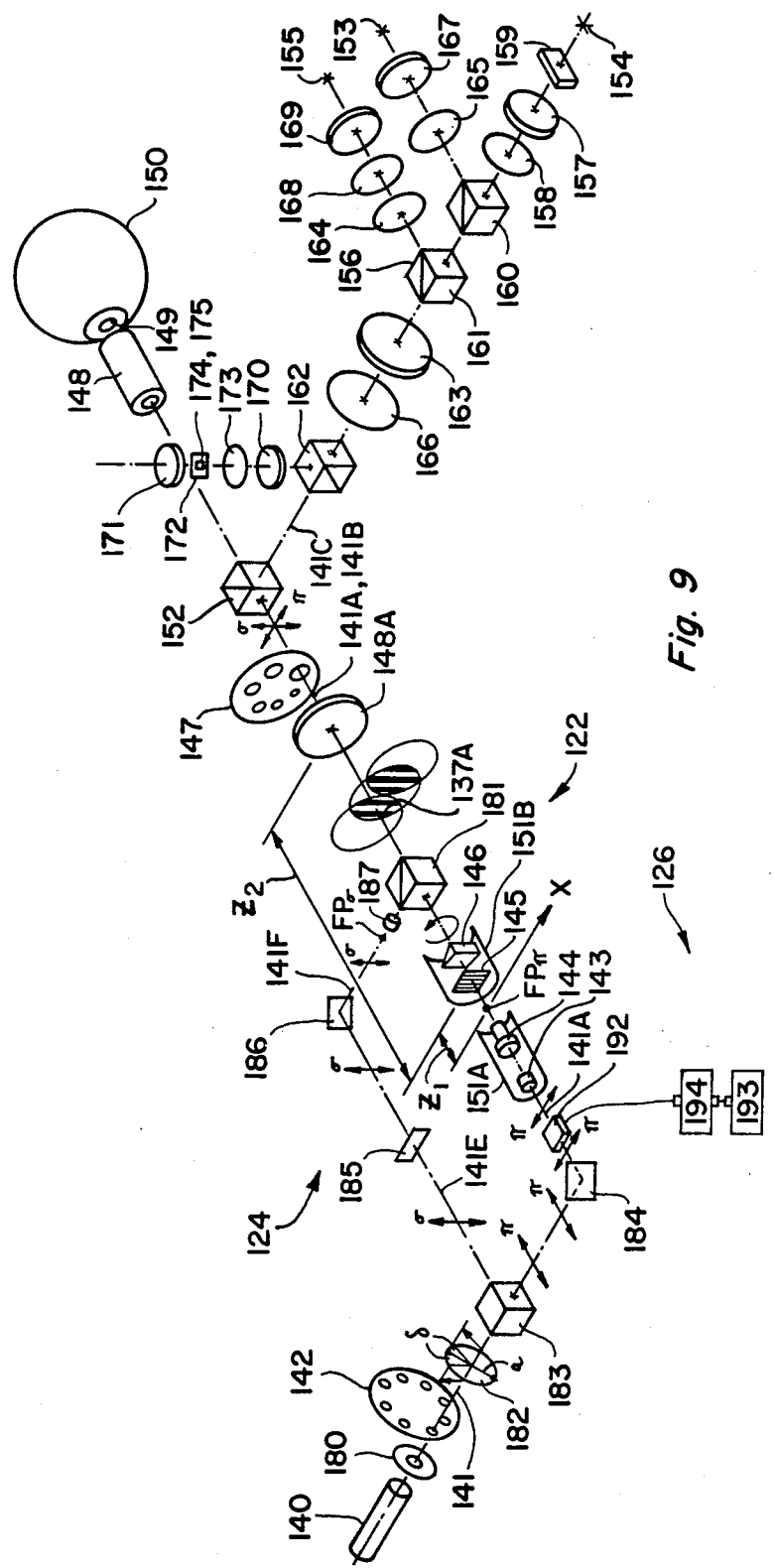
FIG. 9 depicts, in diagrammatic form, ophthalmic testing apparatus for measuring retinal acuity in the central and peripheral regions of the eye, with constant and variable contrast and for providing visual stimuli for visually evoked response measurements.

A retinal acuity instrument utilizing a holographic grating interferometer can perform a variety of acuity measurements in addition to the previously described measurement of central field retinal acuity. FIG. 9 illustrates how optical components can be combined in a system to allow several modes of operation useful in the detection of various eye disorders. More particularly, an acuity perimeter section shown generally at 122 measures peripheral acuity for early detection of glaucoma, a variable contrast testing section indicated generally at 124 permits variable contrast testing to detect eye disorders which impair the ability of the eye to detect low contrast visual stimuli and a visually evoked response (VER) generation section shown generally at 126 helps to diagnose retinal-neurological dysfunction.

Although visually evoked responses (VER), contrast sensitivity, and peripheral acuity have been measured previously, these measurements have been done by methods where the refractive power of the eye could significantly affect the results. In many cases, it is the general neurological retinal response which is impaired by eye diseases and it is necessary to measure the retinal function alone, without abnormalities and variations in the refractive properties of the eye interfering with accurate measurements. Thus, the holographic grating retinal acuity instrument can become a very useful diagnostic instrument because of its ability to by-pass the refractive influence of the eye and to project an interference pattern directly onto the retina. In cases where optical properties of the eye have a negligible effect on measurement of retinal response, laser interference acuity may offer only a convenient method of evaluation. However, in cases where measurement of retinal response is severly impaired by an opacity or refractive abnormality, laser interference acuity becomes a very unique and useful diagnostic tool.

E. Acuity Perimeter

The instrument of FIG. 9 can measure peripheral acuity by projecting interference fringe patterns onto those portions of the retina associated with peripheral vision. Acuity perimetry is particularly useful in the early diagnosis of glaucoma, an eye disorder characterized by deterioration of retinal regions responsible for peripheral vision. Today, as discussed at the outset, testing of peripheral vision is done by flashing light at a variety of locations oblique to the patient's direct line of sight. The patient's ability or inability to detect these flashes of light at different points within a peripheral field of view is directly related to the size of the patient's visual field, but not necessarily to his peripheral acuity.

Wide field retinal acuity testing or acuity perimetry, allows a more quantitative analysis of peripheral vision by flashing a calibrated interference fringe pattern onto those segments of the retina associated with peripheral vision. Natural aberrations of the human eye inhibit the formation of detailed images on peripheral areas of the retina, but the formation of fine interference patterns is unaffected by the eye's refractive errors. Thus, acuity perimetry by means of interference fringes permits quantitative measurement of retinal acuity at eccentric field locations. The ability to resolve peripherally located interference patterns of a particular fineness is a more sensitive test than detecting oblique light flashes because many eye disorders, including glaucoma, cause a loss of peripheral acuity before an actual loss of peripheral sensitivity to light stimulus is evident.

In the FIG. 4 apparatus embodiment described above, a dove prism 46 limits the size of overlap regions 37A and 37B at the aperture wheel 47, thus limiting the maximum field of view provided by the combination of aperture wheel 47 and eyepiece 48. Some relief from field limiting properties of a dove prism can be attained by using a large aperture, high refractive index dove prism, but such a prism is very bulky, expensive, and doesn't offer an optimal solution.

Important differences between the acuity perimeter of FIG. 9 and the FIG. 4 tester are the absence of a dove prism, the addition of collimating lens 148A, andimplementation of fringe field rotation by means of a rotating grating-wedge prism assembly 151B.

Coherent light from a laser 140 propagates along axis 141 and is reflected by a mirror 184 along axis 141A through expander optics to assembly 151B. Housed within assembly 151B are a 400 1/mm optically thin holographic phase grating 145 made as described herein, and a wedge prism 146. The wedge prism simply deviates the fringe field axis, 141B, causing axes 141A and 141B to intersect at the plane defined by aperture wheel 147. Fringe field orientation is changed by rotating assembly 151B about axis 141A, a 360° rotation of that assembly producing a 360° rotation of fringe field 137A. The grating and wedge prism are juxtaposed within the assembly so that axes 141A and 141B are nearly coincident along the entire distance $Z_2$. For all practical purposes, then, the FIG. 9 system is an in-line optical system.

Fringe field 137A propagates along axis 141A, 141B, and fills the aperture of collimating lens 148A. After passing through collimating lens 148A, the fringe field is eventually bounded by one of the apertures in aperture wheel 147. Although the formation of interference fringes on the patient's retina is unaffected by refractive errors of the eye, resolution of a small aperture boundary surrounding the fringe pattern requires nearly normal refraction. Correction of a patient's abnormal refractive error is accomplished by adjusting the position of eyepiece 148 along axis 141A, 141B. The collimating lens 148A insures invariance of the aperture field position during adjustment of element 148 by maintaining a constant chief ray angle at the patient's pupil.

As shown in FIG. 10, the arrangement of lenses 148, 148A and eye pupil 149 constitute an arrangement known as a Maxwellian view. Accurate collimation of spherical waves emanating from the focal point (FP) requires that FP remain at the front focal plane of lens 148A. Therefore, fringe spacing within fringe field 137A is varied by moving assembly 151B to change distance $Z_1$.

In the absence of a dove prism, the dimensions of overlap area 137A are sufficient to fill a large aperture in wheel 147A, or a small aperture located a large distance from axis 141A, 141B. The off-axis position or peripheral field location of the various apertures can be varied by moving the entire wheel assembly in a plane perpendicular to axis 141A, 141B. The maximum distance allowed between that axis and center of an aperture is determined by the f/number of eyepiece 148. Equivalently, the maximum field angle of an aperture presented to a patient is limited by the f/number of eyepiece 148.

The aperture spacing in wheel 147 is chosen to allow only one aperture (target) to appear within the eyepiece field of view at any wheel assembly position. Acuity perimetry requires projection of patterns on small, well defined regions of the retina. Therefore, a small 1° target aperture is most often used during acuity perimetry. Of course, wide field central acuity can be measured by simply locating the aperture wheel assembly at a position which centers the various apertures on axis 141A, 141B.

During peripheral vision testing, the subject sees in Maxwellian view a uniformly illuminated round background field. The background illumination is produced by a white light source 154 which is focused in the subject's entrance pupil, 149. Thus, the amount of background flux entering the eye is independent of pupil diameter. The size of the background is limited by the f/number of the eyepiece 148. Brightness of the background can be varied, allowing acuity testing to be done under either scotopic or photopic conditions. Background source 154 is any convenient, small white light, a preferred embodiment consisting of a pinhole backed by a piece of ground glass and transilluminated by an incandescent lamp.

Still referring to FIG. 9, lens 157 forms an image of source 154 near beamsplitter 160. Lens 163 recollimates the energy passing through beamsplitters 160 and 161, and after propagation through beamsplitters 162 and 152, the aperture of eyepiece lens 148 is filled with a uniform light distribution. Element 148 then refocuses the background flux into the eye pupil 149. The color of the background flux is controlled by color filter 158, a standard colored glass filter being preferred. Background color can be changed by inserting color filters with a variety of bandpass spectra. A preferred method of controlling background intensity is to insert, between the source 154 and lens 157, a variable neutral density wedge 159 driven by a rack and pinion (not shown).

Proper visual fixation is attained by asking the patient to stare at a small fixation source 153, apparently located at the center of the eyepiece field of view defined by axis 141A, 141B. Proper apparent location of source 153 is produced by beamsplitter 152 which directs light from source 153 along axis 141A, 141B into eyepiece 148. Light from source 153 is collimated by lens 167 and passed through linear polarizer 165.

After redirection by cube beamsplitter 160, the fixation beam passes through a beamsplitter 161 and is focused by lens 163 into the focal plane of eyepiece 148. Redirection of fixation source energy by beamsplitter 152 locates the apparent position of the fixation source on axis 141A, 141B, in the same plane as the target apertures. A fixed linear polarizer 166 acts in conjunction with linear polarizer 165 which is rotated to adjust the fixation source intensity observed by the patient. Source 153 can be any convenient small bright source, such as a light-emitting diode, "grain of wheat" bulb or a pinhole transilluminated by an ordinary incandescent light bulb.

After adjustment of a patient's eye position, fixation source intensity and background flux, acuity measurements are initiated by activating the shutter mechanism 180. The shutter action projects a laser interference fringe pattern onto the retina for a controlled period of time. As long as the patient fixates upon source 153, the retinal region, stimulated by the flash of interference fringes, is precisely determined by the eccentricity and meridian coordinates of the target aperture in wheel 147. If a patient resolves the fringe pattern by recognizing the orientation of fringes within the off-axis target aperture, a specific visual acuity at a particular field location is verified.

One of the more obvious sources of error in acuity perimetry is associated with improper eye pupil position just prior to and during target presentation. During testing, the patient's eye pupil should be at the rear focal plane of eyepiece 148 and centered on the axis 141A, 141B to intercept twin coherent point sources.

In an attempt to make appropriate eye position unambiguous, light from the fixation source is constrained by the aperture of lens 167 and enters the eye pupil as a 2 mm collimated beam along the optical axis 141A, 141B. In order to see the fixation source, the subject must adjust the lateral position of his eye pupil to the optical axis 141A, 141B. As already mentioned, background flux is brought to focus at the rear focal plane of eyepiece 148. Therefore, longitudinal adjustment of the eye pupil to the new focal plane of that element is required to accept background flux without vignetting. The criteria for proper eye position are unambiguous, and most subjects naturally seek the correct eye position.

In spite of unambiguous eye position, uncooperative patients should have eye position and fixation monitored by an observation system. Lenses 148 and 170, acting through beamsplitters 152 and 162 constitute an imaging system which forms a real image of the eye surface at image plane 172. A magnified image of the eye surface, including the pupil, can be observed by looking through eyepiece lens 171. Illumination of the eye surface for observation purposes can be generated by illumination source 155.

A preferred embodiment of source 155 is a fairly large ground glass surface, transilluminated by a powerful incandescent lamp. Flux from the groung glass surface of source 155 is approximately collimated by lens 169 and strikes a second ground glass surface 156 which is a ground face of beamsplitter 161. Lenses 163 and 148 collect diffused light from surface 156 and project it onto the eye. A polarizer 168 can be rotated and thus operates in conjunction with fixed polarizer 166 to control the amount of illumination flux reaching the eye.

All of the sources, 153, 154 and 155 produce light which is linearly polarized after passing through linear polarizer 166. Experience has shown that retroreflections from the surfaces of components 162, 152, and 148 can be very distracting to the observer. Therefore, polarizer 166 is fixed with its plane of polarization either perpendicular to or parallel with the plane defined by axes 141A, 141B and 141C. With such an orientation, retroreflections are plane-polarized and can be eliminated by selecting the crossed orientation for linear polarizer 173 in the observation subsystem. Light scattered from the eye surface is in general, randomly polarized and only partially absorbed by polarizer 173.

Further experience has revealed that the large amount of illuminating flux required to observe the eye disturbs the patient's observation of interference patterns. To circumvent this problem, a cut-off filter 164 which blocks visible light and transmits near infrared energy can be placed in the illumination flux subsystem. Subsequently, an infrared image of the eye pupil, free from retroreflections, is formed at plane 172, but illuminating flux is invisible to the patient. Proper fixation can be detected by placing a small infrared sensor 174 at the image plane 172. If the eye is improperly positioned, infrared radiation from the iris and/or sclera will be detected by the infrared sensor. When the patient's pupil is properly positioned, an image of the relatively dark pupil will fall on the detector with the absence of a detector signal indicating proper eye pupil location.

A magnified infrared image of the pupil formed by lens 170 can be formed directly on the detector 175 of a commercially available TV camera at the location of detector 174. Fixation can then be monitored directly by observing the patient's pupil on a television screen.

F. Variable Contrast—Mode I

It is a well known fact that many eye disorders impair the ability to resolve low contrast visual stimuli. Since the FIG. 9 instrument provides a visual stimulus directly to the retina, the ability to control the contrast of the stimulus would greatly increase the sensitivity of various diagnostic procedures, including acuity perimetry and central field response. Section 124 of that instrument provides that capability. Variable contrast interference patterns can be generated by using a linearly polarized laser 140 and exploiting the invariant response of the optically thin holographic grating 145 to coherent radiation in different states of polarization.

Still referring to FIG. 9, a linearly polarized laser beam from the laser travels through an open shutter 180 and through a neutral density filter wheel 142 to a "half wave plate" or half wave retarder 182. The arrows extending from axis 141 indicate rotation of the polarization plane after passage through half wave retarder 182. The optical axis (a) of plate 182 is indicated by two dots and as known in the art, the output plane of polarization is rotated through twice the angle between the input plane of polarization and the retarder optical axis. Polarizing beamsplitter 183 splits the incoming linearly polarized beam into two, orthogonally polarized components π and σ. The π component of the input beam is transmitted to mirror 184, while the σ component is reflected along axis 141E, through compensating filter 185 and to mirror 186. The relative intensity of the π and σ beams is governed by the optical axis orientation of half wave plate 182. If the input beam to beamsplitter 183 is in a pure σ polarization state, the transmitted beam intensity will be effectively zero and reflected beam intensity will be a maximum. Similarly, if the input beam at splitter 183 is in a pure π polarization state, the transmitted beam intensity will be a maximum and reflected beam intensity will be effectively zero.

The π polarized beam proceeds through the acuity perimeter section 122 via mirror 184 and is responsible for the fringe field 137A and the interference pattern eventually formed on the patient's retina. Cube beamsplitter 181 transmits a significant portion of the polarized fringe field to collimating lens 148A and aperture wheel 147. Because of the common path nature of the holographic grating interferometer, fringe field 137A suffers insignificant distortion during transmission to the aperture wheel. Of importance is the preservation of π polarization after diffraction by the optically thin, holographic grating 145. Eyepiece 148 finally focuses the π polarized waves in fringe field 137A and forms the coherent π polarized sources within the patient's eye pupil 149.

The σ polarized beam eventually reaches the refractive element 187 which is properly located to form point source FP$_\sigma$ at the front focal point of lens 148A. Element 187 can be either a positive or negative lens, the primary requirement being sufficient power to eventually diverge the σ beam enough to fill the apertures within wheel 147 with a uniform wavefront. Cube beamsplitter 181 redirects the σ polarized wave toward collimation lens 148A and aperture wheel 147 without altering the state of polarization. Eyepiece 148 focuses the σ polarized wavefront to a point source at the eye pupil.

In general, the eye pupil now contains three point sources, two from π polarized waves and one from a σ polarized wave. The π polarized wavefronts propagating back through the eye 150 toward the retina, interfere and are responsible for the fringe pattern projected onto the retina. The σ polarized wavefront also propagates back through the eye, but fails to interact (interfere) with the orthogonally polarized π wavefronts. Therefore, the σ polarized wave provides a background irradiance which can be simply added to the fringe pattern irradiance.

When the relative intensity of the σ polarized wavefront is high, background illumination dominates and the fringe pattern seen by the patient has low contrast. If the π polarized wavefronts are dominant, the fringe pattern seen by the patient is superimposed upon a relatively low level background, thus producing a high contrast pattern. Fringe pattern contrast is controlled simply by rotation of the half wave plate 182. Element 185 is a variable neutral density filter which preserves the σ polarized state of the background beam and equalizes the maximum average retinal irradiance from the σ and π polarized wavefronts. With the filter 185 correctly adjusted, the average retinal irradiance I from both σ and π wavefronts remains constant at any fringe pattern contrast. The standard definition of fringer pattern contrast C is:

$$C = \frac{I \max - I \min}{I \max + I \min} \quad (3)$$

When filter 185 is adjusted to maintain a constant average retinal irradiance, the contrast C varies according to the formula:

$$C = \frac{(\sin 2\delta)^2}{1 + (\cos 2\delta)^2} \quad (4)$$

where δ is the rotation angle of the half wave plate 182.

G. Variable Contrast—Mode II

The instrument depicted in FIG. 11 can produce a variable contrast fringe pattern in another mode of operation which uses polarized light and the invariant response of an optically thin holographic grating 145 to coherent radiation in different states of polarization. Many of its components are common to the instrument shown in FIG. 9 and these carry the same identifying numerals.

Operation of the FIG. 11 embodiment relies upon a double refraction element such as a Rochon or Wollaston prism 192 to generate orthogonally polarized σ and π beams. The Wollaston or Rochon prism 192 deviates the σ and π laser beam components at slightly different angles and the expander assembly 151A forms two spatially separated point sources FP$_\sigma$ and FP$_{90}$. In both the FIG. 9 and FIG. 11 embodiments, the action of half wave plate 182 controls the relative intensity of sources FP$_\sigma$ and FP$_\pi$.

Holographic grating 145 generates two independent fringe fields and wedge prism 146 directs these fields into the overlap area 137A. One fringe field in area 137A is π polarized, emanating from FP$_\pi$, while the second fringe field in area 137A is σ polarized, emanating from FP$_\sigma$. The two fringe field irradiances are superimposed as shown and fail to interfere because of their mutually perpendicular states of polarization. The angle between the σ and π beams is determined by the refracting angle of the Wollaston or Rochon prism 192.

The lateral distance X between FP$_\sigma$ and FP$_\pi$ can be controlled by adjusting the spacing d between negative lens 143 and objective 144. In a situation similar to the one described in my U.S. Pat. No. 4,265,534 with respect to FIG. 11A therein, the σ and π polarized fringe fields are shifted with respect to each other as the lateral distance X between FP$_\sigma$ and FP$_\pi$ varies. For variable contrast operation, the shift between σ and π fringe fields is set and locked at 180° by an adjustment of spacing d and distance X. It is important to note that the phase shift is a function of distance X only and is independent of $Z_1$.

Changing the fringe field orientation by means of rotating the assembly 151A will change the phase shift between the σ and π fields within area 137A unless the separation X between FP and FP remains constant and perpendicular to the grating structure within holographic grating 145. Invariance of the FP$_\sigma$, FP$_\pi$ separation, perpendicular to the grating structure is achieved by rotating element 192 about axis 141. Rotation of element 192 is simply geared at a 1:1 ratio with the rotation of assembly 151B to maintain proper orientation between FP$_\sigma$, FP$_\pi$ and the structure of grating 145. With a 180° phase shift between the σ and π fringe fields, the irradiance distribution of the fringe pattern projected out to the aperture wheel and eventually onto the retina becomes:

$$I = I_o(\sin 2\delta)^2 \sin^2 x + I_o(\cos 2\delta)^2 \cos^2 x \qquad (5)$$

where $I_o (\sin 2\delta)^2$ and $I_o (\cos 2\delta)^2$ are the intensities of the $\sigma$ and $\pi$ beams as controlled by the half wave plate 182.

When the half wave plate is rotated through $\delta = 22.5°$, $I_o (\sin 45°)^2 \approx I_o (\cos 45°)^2$ and the fringe pattern shows no spatial modulation or zero contrast. When either $I_o (\sin 2\delta)^2$ or $I_o (\cos 2\delta)^2$ is equal to zero, the pattern seen by the patient has a maximum contrast of 1. The formula relating contrast to rotation angle $\delta$ of the half wave plate is:

$$C = (\sin 2\delta)^2 - (\cos 2\delta)^2 \qquad (6)$$

H. Visually Evoked Response Pattern Generation—Mode I

The variable contrast control provided by rotation of the half wave plate 182 in FIG. 11 produces a phase reversing fringe pattern when the half wave plate is rotated at a constant angular velocity by a synchronous motor acting through a belt drive (not shown). During one revolution of the half wave plate 182, the fringe pattern appears as a $\cos^2 X$ irradiance distribution at $\delta = 0°, 90°, 180°$ and $270°$. The fringe pattern appears as a $\sin^2 X$ distribution at $\delta = 45°, 135°, 225°$ and $315°$.

Neurological response to a time varying, phase reversing stimulus can be measured with the aid of electronic equipment. Measurement of evoked potentials (EP) is very useful in the diagnosis of retinal-neurological dysfunction. The response to a time varying visual stimulus is an electrical signal sent to the brain via the optic nerve. The electrical signal or evoked potential EP is detected by electrodes (not shown) attached to the subject's scalp. Synchronization of the visual stimulus with a signal averager (not shown) permits extraction of the very weak EP signal from other "brain waves". The EP measurements can also be made on newborn infants and unresponsive patients because confirmation of pattern recognition does not require communication with the patient.

Today, the most common time varying visual stimulus presented to a patient is a phase-reversing checkerboard pattern or a phase-reversing bar pattern on a television screen. Research has shown that human visual evoked responses (VER) produced by patterned stimuli are highly dependent upon retinal image quality. In other words, VER is highly dependent upon how well the patient can see the television screen that is generating the visual stimuli. Therefore, the instrument shown in FIG. 11 modified to rotate plate 182 to generate phase reversing patterns is an ideal generator of patterned stimuli, remembering that the clarity of laser interference fringe patterns projected onto the retina is unaffected by refractive errors of the eye.

I. Visually Evoked Response Pattern Generation—Mode II

Another method of generating well synchronized, time varying visual stimuli on the retina involves insertion of an acousto-optic deflector 192 along axis 141A of the instrument depicted in FIG. 9. The acousto-optic deflector, a commercially available device, deflects the laser beam back and forth in the X direction at a frequency determined by an electrical waveform generator 193 which controls the deflector by way of a commercially available driver 194. Acousto-optic beam deflection changes the X coordinate of $FP_\pi$ and causes fringe field 137A to shift. A thorough explanation of pattern motion within field 137A caused by changing the relative position of FP and the holographic grating can be found in my U.S. Pat. 4,265,534.

The temporal characteristics and magnitude of the fringe field shift are controlled by the waveform generator 193 and modulator driver 194. The visual stimulus produced by the FIG. 9 instrument operating in this Mode II, constitutes a pattern phase shift, while the stimulus produced by rotation of the half wave plate 182 in the FIG. 11 instrument in Mode I, is a pattern phase reversal. From a medical point of view, the advantages and disadvantages of Mode I vs. Mode II stimuli are unclear at the present time.

J. Visually Evoked Response Pattern Generation "Laser Checkerboard".

The general consensus of opinion is that a phase shifted or phase reversed rectilinear pattern provides less visual stimulation than a phase reversed or phase shifted "cross-hatched" or checkerboard pattern. Therefore, a preferred laser visually evoked response (VER) instrument should be capable of producing a two dimensional, phase shifted interference pattern.

Figure 12:
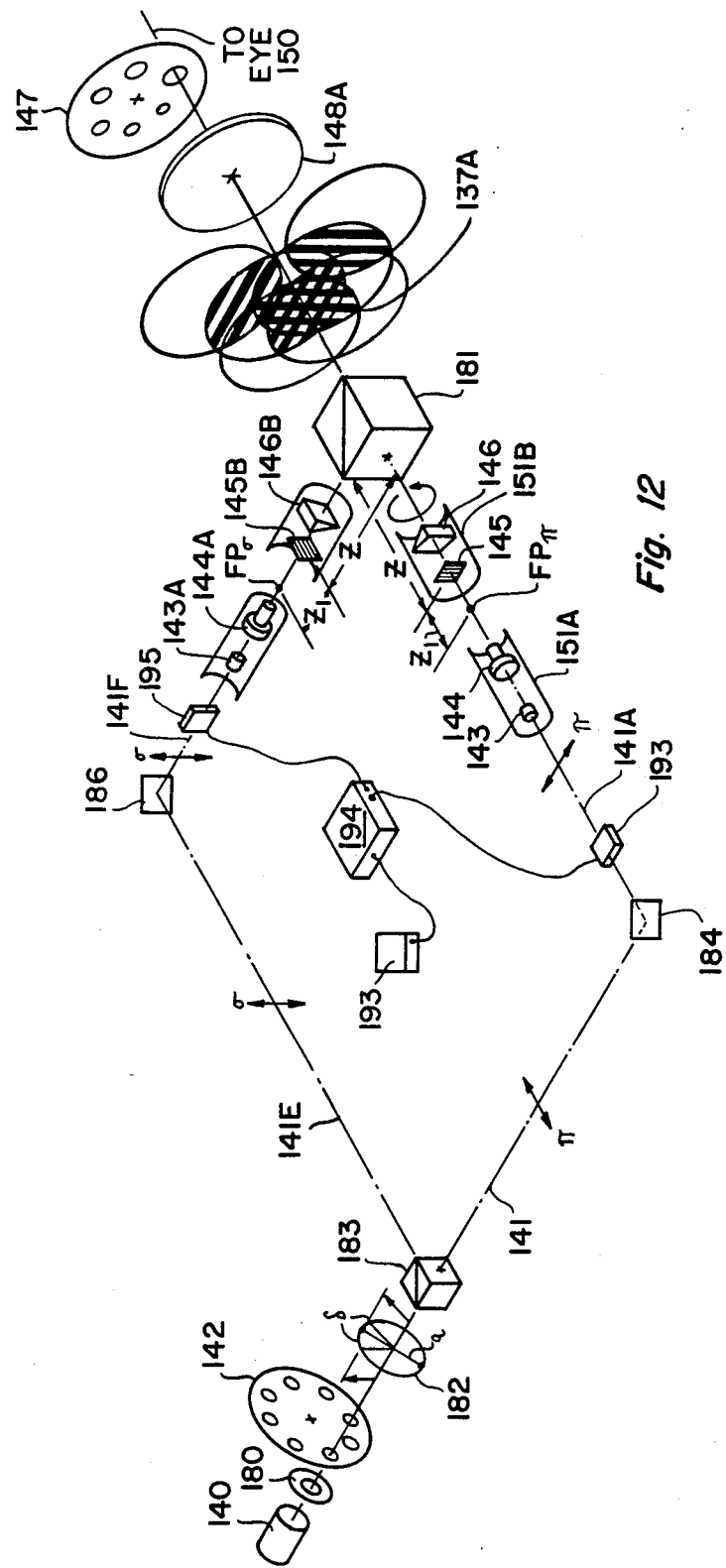
FIG. 12 depicts, in diagrammatic form, another embodiment of ophthalmic testing apparatus for providing another type of stimuli for visually evoked response measurements.

Operating in accordance with the principles explained in the description of Variable Contrast Mode I, and Visually Evoked Pattern Generation Mode II, a laser checkerboard (VER) stimulator shown in FIG. 12 can generate a phase shifted, laser checkerboard pattern, i.e., a pattern of superimposed horizontal and vertical fringes. Here again, this unit has many elements in common with the earlier described ones and carries the same identifiers.

In the FIG. 12 apparatus, the $\sigma$ polarized beam passes to mirror 186, through an acousto-optical deflector 195, through lenses 143A and 144A and eventually forms source $FP_\sigma$ at the front focal plane of a collimating lens 148A. Holographic grating 145B and wedge prism 146B are located at the same variable distance $Z_1$ from $FP_{94}$, thereby producing $\sigma$ polarized horizontal fringes of the same spatial frequency as the $\pi$ polarized vertical fringes. Deflector 195, grating 145B, and wedge prism 146B are properly oriented to accommodate shifting of the $\sigma$ polarized horizontal fringes in the vertical direction.

Again, since thin holographic gratings 145, 145B and cube 181 preserve the polarization state of original $\sigma$ and $\pi$ beams, the superimposed, horizontal and vertical fringes at aperture wheel 147 propagate without interaction. Both acousto-optical deflectors 192 and 195 can be driven by the function generator 193, thus shifting the horizontal and vertical fringe pattern in a synchronous manner to provide a phase shifted "laser checkerboard" visual stimulus.

K. Focimeter

The optical system which constitutes the basic retinal acuity tester depicted in FIG. 3 can also be used as a focimeter; i.e., an instrument which detects the focal point of, and measures the focal length of, a lens. The basic phase grating interferometer shown in FIG. 3 produces fringes in the areas of overlap whose spacing is governed by the Equation (2) above. As seen from this equation, $T \to \infty$ as $Z_1 \to 0$. Therefore, a very broad or null fringe appears in the overlap areas when the focal point FP lies on the grating surface. Once the focal point is located on the grating surface, a straightforward measurement of the distance between the grating and the lens housing yields the back focal length of the lens.

One practical approach to the design of a phase grating focimeter involves the construction of a reference optical system with minimal spherical aberration, well specified foci, and a numerical aperture compatible with grating frequency. Once the reference optical system is built, the foci can be located by means of the holographic phase grating. The test lens can then be inserted into the reference optical system at a specified plane and the resulting change in focal distance of the reference system plus the test lens can be measured with the phase grating. Since all parameters of the reference system are specified, the measured change in focus can be used to calculate the focal length of the test lens.

A specific embodiment of a phase grating focimeter is shown in FIGS. 3 and 3A, the optical elements shown in FIG. 3A being placed on the optical axis 31 ahead of grating 34 as depicted in FIG. 3. As seen there, the microscope objective 33 forms a point source FP at the unit magnification plane, which is a distance of 2 focal lengths from lens 38. A test lens 39 is placed between objective 33 and lens 38. Lens 38 is a four-element lens which is designed to image FP at FP' with minimal spherical aberration. In one embodiment, lens 38 is a 30 mm focal length symmetrical lens consisting of two optimized achromats mounted "back to back" to minimize spherical aberration. Lens 38 should also possess significantly greater power than the test lens 39 to prevent the test lens from forming image FP' in front of lens 38.

When a spherical wave from source FP' strikes the grating 34, a number of cones of diffraction are produced. Of particular interest are cones 35, 36A and 36B which overlap and produce fringes in areas 37A and 37B. The fringe spacing in overlap areas 37A and 37B can be calculated from Equation (2).

The point FP' can be located on the surface of the holographic grating 34 by translating the grating and observing the fringe patterns in areas 37A and 37B. When $Z_1 \rightarrow 0$, $T \rightarrow \infty$ and a very broad or null fringe is observed. With the grating 34 located at the null fringe position, a test lens 39 can be inserted at the front focal plane of lens 38. Placing the test lens at the front focal plane of lens 38 leaves the optical power of the system unchanged, but alters the back focal length and therefore the position of FP'. The change in $Z_1$ caused by insertion of a test lens is:

$$\Delta Z_1 = \frac{f^2}{f_t} \tag{7}$$

where f is the focal length of lens 38 and $f_t$ is the focal length of the test lens.

The focal length of the test lens can be determined simply by measuring the subsequent grating displacement $\Delta Z_1$ required to regenerate a null fringe pattern. Since f is known and $\Delta Z_1$ can be measured directly by measuring grating 34 translation, the focal length $f_t$ can be calculated directly from Equation (7).

One particularly useful modification of the FIGS. 3 and 3A apparatus involves testing of aspheric lenses. Reference lens 38 can be constructed of basically simple spherical elements with radii of curvature and spacings selected to image FP at FP' with a calculable amount of aberration. Initially, the fringes within areas 37A and 37B will depart from a straight line or null pattern due to the aberrations of reference system 38. However, if the aberrations introduced by lens 38 are of opposite mathematical sign to those generated by an aspheric test lens 39, the fringes within areas 37A and 37B will revert back to a null pattern upon insertion of the aspheric test lens. Such a null system is particularly useful for testing intraocular lenses. The ideal intraocular lens implanted into the human eye is an aspheric element with a modest amount of asphericity, easily "nulled" by a relatively simple reference lens 38 in the FIGS. 3 and 3A apparatus.

In another mode of operation, grating 34 is positioned and remains stationary at an original null fringe position. Insertion of a test lens 39 results in the generation of a fringe pattern in overlap areas 37A and 37B. The fringe spacing depends upon the power of test lens 39 as related by $$\frac{f^2(T\xi - 1)}{Z_2} = f_t \tag{8}$$

where T is the fringe period associated with insertion of the test lens 39, $\xi$ is the grating frequency, f is the focal length of reference lens 38, $f_t$ is the focal length of the test lens, and $Z_2$ is the projection distance shown in FIG. 3. Typical values of the quantities in Equation (8) are f=30 mm, $\xi$=200 l/mm; $Z_2$=100 mm. These values yield T=0.116 mm, when $f_t$=200 mm. The fringe period can be measured electronically with a scanning photodetector or visually with the aid of an eyepiece and reticle.

Today, many focimeters yield data by relying on operator judgment to align and focus optical patterns. Data gathered from such measurement oftentimes lacks the desired accuracy and repeatability required in focimetry. Whatever method of fringe measurement chosen, the present grating focimeter offers the advantage of presenting an unambiguous pattern from which quantitative measurements can be made.

Another important consideration in the operation of a phase grating focimeter is the testing of lenses which have considerable aberration. Lens aberrations result in the formation of an imperfect point source at FP' resulting in the formation of fringe patterns in areas 37A and 37B which depart significantly from straight lines, e.g. shearing interferograms which are patterns that can be deciphered to yield quantitative information about wavefront deformations associated with lens aberrations.

With phase grating focimetry, the longitudinal adjustment of grating 34 results in the generation of paraxial focus, mid-focus and marginal focus fringe patterns. The distance between grating positions for generation of paraxial, mid- and marginal focus interferograms is a direct measure of the test lens spherical aberration. The same procedure of moving the grating 34 to find various zonal foci can also provide a direct measure of the asphericity of the test lens.

When an ophthalmic lens is attached to a rotating means, the axis of any cylinder power can be oriented with the grating to produce the patterns shown in FIG. 3. The focal length of a preferred axis can be measured by aligning the grating with the cylinder axis and "nulling" the fringes along the preferred axis as shown in that figure. The practicality of using a phase grating focimeter to test severely aberrated lenses is determined by the complexity of the generated fringe patterns and the method of fringe detection.

In summary, there has been disclosed herein a basic interferometer construction that utilizes a holographically recorded grating for projecting stable, high-contrast fringe patterns with high efficiency for testing retinal acuity. It will be apparent from the foregoing discussion, however, that the specific embodiments of this invention that have been disclosed are merely representative. The basic principles can be employed in a wide variety of applications with the attainment of some or all of the advantages of this invention. One important point to remember is that the grating must be optically thin so that, when polarized light sources are used, the grating does not change the state of polarization. Therefore, it is an object of the appended claims to cover all such variations and modifications as come within the true spirit and scope of this invention.

What I claim as new and desire to secure by Letters Patent of the United States is:

1. Opthalmic apparatus for producing an interference pattern on the retina of an eye, said apparatus comprising:
   A. interference pattern generating means for generating a first diffraction and a second diffraction that have equal strength, that overlap and the absolute values of whose order numbers are different thereby to produce a high-contrast, low-noise interference pattern in the area of overlap;
   B. focusing means positioned on an axis to receive the interference pattern from said interference pattern generating means for projecting the interference pattern onto the retina from only two point sources of light in the eye pupil; and
   C. means for affecting the interference pattern produced on the retina.

2. Apparatus as recited in claim 1 wherein said interference pattern generating means includes:
   A. spatially coherent light source means; and
   B. holographically recorded, optically thin, single frequency phase grating means responsive to the energy from said light source means for producing the diffractions.

3. Apparatus as recited in claim 2 wherein the light source means is quasi-monochromatic.

4. Apparatus as recited in claim 2 wherein said affecting means includes optical means between the grating means and the focusing means for rotating the interference pattern produced on the retina.

5. Apparatus as recited in claim 4 wherein the optical means comprises dove prism means.

6. Apparatus as recited in claim 2 wherein said affecting means comprises:
   A. second focusing means between said light source means and said grating means for focusing the light at a focal point that is displaced along said axis toward said light source means from said grating means; and
   B. positioning means acting between said second focusing means and said grating means for moving the focal point along said axis with respect to the grating means thereby to vary the interference pattern.

7. Apparatus as recited in claim 6 wherein said positioning means connects to said second focusing means and said second focusing means includes:
   A. negative lens means for receiving light from said light source means;
   B. objective lens means for focusing light from said negative lens means at the focal point; and
   C. filter means connected between said light source means and said negative lens means for varying the intensity of the light from said light source means.

8. Apparatus as recited in claim 2 wherein said focusing means comprises:
   A. eyepiece means; and
   B. aperture means positioned between said grating means and said eyepiece means.

9. Apparatus as recited in claim 8 and additionally comprising optical viewing means interposed between said eyepiece means and said grating means for enabling the viewing of the eye through said eyepiece means.

10. Apparatus as recited in claim 9
    A. wherein the interference pattern from said grating means is projected along said axis; and
    B. said optical viewing means comprises:
       (1) beamsplitting means disposed on said axis between said grating means and said eye piece means;
       (2) second light source means for projecting light orthogonally to said axis to said beamsplitting means, said beamsplitting means thereby directing the light through said eyepiece means to that eye; and
       (3) viewing means for receiving reflected light from said eyepiece means through said beamsplitting means for viewing the eye.

11. Apparatus as recited in claim 10 wherein said viewing means comprises cross polarizing means on said axis.

12. Apparatus as recited in claim 10 wherein said optical viewing means includes:
    A. second beamsplitting means disposed on said axis between said first beamsplitting means and said grating means;
    B. second eyepiece means aligned on a viewing axis intercepting said second beamsplitting means and said axis;
    C. first and second cross polarizing means disposed on the viewing axis between said second eyepiece means and said second beamsplitting means and on said axis between said grating means and said second beamsplitting means;
    D. lens means disposed between said first cross polarizing means and said second beamsplitting means for producing a viewable image; and
    E. mirror means disposed on an extension of the viewing axis on a side of said second beamsplitting means opposite to said lens means.

13. Apparatus as recited in claim 8 wherein said focusing means additionally comprises:
    A. dove prism means disposed on said axis between said grating means and said eyepiece means; and
    B. means for rotating said dove prism means thereby to rotate the interference pattern produced on the retina.

14. Apparatus as recited in claim 6 and further including means disposed between the light source means and the second focusing means for selectively deflecting the light from the source means in a plane perpendicular to said axis so as to shift the interference pattern.

15. Apparatus as defined in claim 14 wherein the deflecting means includes
    A. an acousto-optic deflector; and
    B. waveform generating means connected to drive the deflector.

16. Apparatus as recited in claim 6 and further including
   A. second focusing means between the light source means and the grating means;
   B. reference lens means between the second focusing means and the grating means; and
   C. means for positioning an ophthalmic test lens between the second focusing means and the reference lens means.

17. Apparatus as recited in claim 16 and further including means for adjusting the spacing along said axis between the grating means and the positioning means.

18. Apparatus as recited in claim 16 and further including means for rotating a test lens positioned in the positioning means about said axis.

19. Apparatus as defined in claim 2 and further comprising
   A. second focusing means between the light source means and the grating means for focusing the light at a focal point that is displaced along said axis toward said light source means from said grating means;
   B. light deflecting means positioned on said axis a fixed distance beyond said grating means for deflecting light from the light source means off said axis;
   C. means for adjusting the position of the grating means and light deflecting means in unison along said axis;
   D. light collimating means located between said grating means and said focusing means;
   E. aperture means positioned off said axis between the collimating means and the focusing means for exposing the interference pattern to a peripheral region of the retina; and
   F. means located between the light source means and the focusing means for interrupting the light from the light source means.

20. Apparatus as defined in claim 19 and further including means for moving the aperture means so as to permit selection of said peripheral region.

21. Apparatus as defined in claim 19 wherein said affecting means includes means for rotating said grating means and said deflecting means in unison about said axis.

22. Apparatus as defined in claim 19 wherein the deflecting means comprises a wedge prism.

23. Apparatus as defined in claim 19 wherein the aperture means comprises a member
   A. having a plurality of different size apertures; and
   B. means for moving said member to position said apertures off axis to expose light from the collimating means to the selected peripheral region.

24. Apparatus as defined in claim 19 and further including means for moving the focusing means along said axis.

25. Apparatus as defined in claim 19 and further including
   A. fixation light source means; and
   B. means for imaging light from said fixation light source means onto said retina.

26. Apparatus as defined in claim 25 wherein the fixation light source means comprises
   A. beamsplitting means positioned on said axis between the aperture means and said focusing means;
   B. second light source means for projecting light orthogonally to said axis to said beamsplitting means whereby to direct that light through said focusing means to the eye; and
   C. light collimating means between the second source means and said beamsplitting means.

27. Apparatus as defined in claim 25 and further including means for adjusting the intensity of the light from the fixation light source means.

28. Apparatus as defined in claim 27 wherein the intensity adjusting means comprises polarizing means positioned between the second light source means and the beamsplitting means.

29. Apparatus as defined in claim 19 and further including means for focusing light on the pupil of said eye so as to excite said retina to provide a uniform background illumination field.

30. Apparatus as defined in claim 29 and further including means for varying the intensity of the background illumination field.

31. Apparatus as defined in claim 30 and further including means for monitoring the position of the eye at which the interference pattern is produced.

32. Apparatus as defined in claim 31 wherein the position monitoring means includes
   A. optical means for focusing a real image of the eye surface onto an image plane; and
   B. variable intensity light source means for illuminating said eye surface.

33. Apparatus as defined in claim 19 and further including
   A. means for providing a background irradiance which is superimposed on said interference pattern projected onto said retina; and
   B. means for varying the relative intensity of the interference pattern and the background irradiance so as to vary the contrast of the interference pattern.

34. Apparatus as defined in claim 33 wherein the irradiance providing means includes
   A. polarizing beamsplitting means disposed between the light source means and the second focusing means for splitting the light from the light source means into first and second differently polarized light components, the former of which produces the interference pattern and the latter of which produces the background irradiance;
   B. means disposed between the grating means and the focusing means for combining the first light component from the grating means with the second light component from the beamsplitting means so that said light components are superimposed in said area of overlap; and
   C. means for varying the relative intensity of said light components.

35. Apparatus as defined in claim 34 wherein the intensity varying means includes light retarding means disposed between the light source means and the beamsplitting means.

36. Apparatus as defined in claim 34 wherein the light retarding means includes a half wave plate.

37. Apparatus as defined in claim 6 and further including
   A. means for producing a second interference pattern in said area of overlap which is superimposed on, but is phase shifted with respect to, the first interference pattern; and
   B. means for varying the relative intensity of said first and second interference patterns.

38. Apparatus as defined in claim 37 wherein said intensity varying means includes
  A. light retarding means disposed between the light source means and the second focusing means;
  B. light polarizing means disposed between the light retarding means and the second focusing means for splitting the light from the light source means into first and second differently polarized light components, one of which produces the first interference pattern and the other of which produces the second interference pattern; and
  C. means for rotating said light polarizing means and said grating means in unison about said axis so as to change the relative intensity of said first and second light components.

39. Apparatus as defined in claim 38 wherein:
  A. the retarding means comprises a half wave plate; and
  B. the polarizing means includes double light refracting means disposed on said axis.

40. Apparatus as defined in claim 39 and further including means for rotating the double light refracting means about said axis so as to vary the relative intensity of said interference patterns in a continuous fashion.

41. Apparatus as defined in claim 6 and further including
  A. means for producing a second interference pattern in said area of overlap which is superimposed on, and is oriented at an angle with respect to, the first interference pattern; and
  B. means for varying the intensities of the first and second interference patterns in unison.

42. Apparatus as defined in claim 41 wherein the second interference pattern producing means includes
  A. light retarding means disposed between the light source means and the second focusing means;
  B. light polarizing beamsplitting means disposed between the retarding means and the second focusing means for splitting said light into first and second differently polarized light components, the former of which travels along said axis and produces the first said interference pattern, the latter of which follows a second axis;
  C. second grating means similar to the first positioned on the second axis;
  D. third focusing means positioned on the second axis beyond the second grating means for focusing the second light component at a focal point that is displaced along the second axis from the second grating means;
  E. means disposed between the first and second grating means and the focusing means for combining the first light component from the first grating means with the second light component from the second grating means so that said components produce superimposed orthogonal interference patterns in said area of overlap; and
  F. means for selectively shifting said interference patterns in unison.

43. Apparatus as defined in claim 42 wherein the shifting means comprises
  A. first light deflecting means disposed on the first axis ahead of the second focusing means;
  B. second light deflecting means disposed on the second axis ahead of the third focusing means; and
  C. means for operating said deflecting means so as to deflect simultaneously said first and second light components in orthogonal directions in planes perpendicular to their axes.

* * * * *